(12) United States Patent
Dorchak et al.

(10) Patent No.: US 6,582,437 B2
(45) Date of Patent: Jun. 24, 2003

(54) DEVICES AND METHODS FOR IMPLANTING FUSION CAGES

(75) Inventors: John D. Dorchak, Midland, GA (US); Eddie F. Ray, III, Collierville, TN (US); John L. White, Bartlett, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 167 days.

(21) Appl. No.: 09/790,926

(22) Filed: Feb. 22, 2001

(65) Prior Publication Data

US 2001/0031968 A1 Oct. 18, 2001

Related U.S. Application Data

(63) Continuation of application No. 09/649,696, filed on Aug. 28, 2000.
(60) Provisional application No. 60/150,787, filed on Aug. 26, 1999.

(51) Int. Cl.$^7$ ............................................. A61B 17/88
(52) U.S. Cl. ............................................ 606/90; 606/57
(58) Field of Search ..................................... 606/57, 90

(56) References Cited

U.S. PATENT DOCUMENTS

| | | | |
|---|---|---|---|
| 5,015,255 A | 5/1991 | Kuslich | 623/17 |
| 5,055,104 A | 10/1991 | Ray | 606/61 |
| 5,431,658 A | 7/1995 | Moskovich | 606/99 |
| 5,484,437 A | 1/1996 | Michelson | 606/61 |
| 5,489,307 A | 2/1996 | Kuslich et al. | 623/17 |

(List continued on next page.)

FOREIGN PATENT DOCUMENTS

| | | |
|---|---|---|
| EP | 0716840 A2 | 6/1996 |
| EP | 0880938 A1 | 12/1998 |
| WO | WO 96/40020 | 12/1996 |
| WO | WO 99/09896 | 3/1999 |
| WO | WO 99/09913 | 3/1999 |
| WO | WO 99/52453 | 10/1999 |
| WO | WO 00/041654 | 7/2000 |
| WO | WO 00/041655 | 7/2000 |
| WO | WO 00/45709 | 8/2000 |

OTHER PUBLICATIONS

*Reduced Profile Instrumentation Surgical Technique*, as described by J. Kenneth Burkus and John D. Dorchak, M.D.; Sofamor Danek, ©1999.
*Anterior Instrumentation Surgical Technique*, as described by Scott H. Kitchel, M.D.; Sofamor Danek, ©1999.

*Primary Examiner*—Cary E. O'Connor
*Assistant Examiner*—Candice C. Melson
(74) *Attorney, Agent, or Firm*—Woodard, Emhardt, Moriarty, McNett & Henry LLP

(57) ABSTRACT

Methods and instrumentation for spinal interbody fusion are disclosed. The instruments and methods are particularly adapted for interbody fusion in an unreamed disc space. One instrument is a distractor assembly including a first distractor and a second distractor configured to be inserted in side-by-side relation in the disc space. Fusion cages adapted for insertion into an unreamed disc space are provided to enhance load distribution between adjacent vertebral bodies and lateral stability of the spinal column. The fusion cages may be inserted after distracting the disc space with the distractor assembly. Instruments for preparing the disc space through the inserted fusion cages or for use with the distractor assembly are also provided.

31 Claims, 18 Drawing Sheets

U.S. PATENT DOCUMENTS

| | | | |
|---|---|---|---|
| 5,505,732 A | 4/1996 | Michelson | 606/61 |
| 5,556,399 A | 9/1996 | Huebner | 606/80 |
| 5,571,109 A | 11/1996 | Bertagnoli | 606/61 |
| 5,609,635 A | 3/1997 | Michelson | 623/17 |
| 5,609,636 A | 3/1997 | Kohrs et al. | 623/17 |
| 5,683,463 A | 11/1997 | Godefroy et al. | 623/17 |
| 5,720,748 A | 2/1998 | Kuslich et al. | 606/80 |
| 5,741,253 A | 4/1998 | Michelson | 606/61 |
| 5,759,185 A | 6/1998 | Grinberg | 606/80 |
| 5,772,661 A | 6/1998 | Michelson | 606/61 |
| 5,782,919 A | 7/1998 | Zdeblick et al. | 623/17 |
| 5,785,710 A | 7/1998 | Michelson | 606/61 |
| 5,797,909 A | 8/1998 | Michelson | 606/61 |
| 5,865,834 A | 2/1999 | McGuire | 606/80 |
| 5,865,847 A | 2/1999 | Kohrs et al. | 623/17 |
| 5,885,287 A | 3/1999 | Bagby | 606/61 |
| 5,885,299 A | 3/1999 | Winslow et al. | 606/99 |
| 5,888,227 A | 3/1999 | Cottle | 623/17 |
| 5,899,908 A | 5/1999 | Kuslich et al. | 606/96 |
| 5,947,971 A | 9/1999 | Kuslich et al. | 606/80 |
| 5,968,098 A | 10/1999 | Winslow | 623/17 |
| 6,004,326 A | 12/1999 | Castro et al. | 606/99 |
| 6,033,405 A | 3/2000 | Winslow et al. | 606/61 |
| 6,042,582 A | 3/2000 | Ray | 606/61 |
| 6,056,749 A | 5/2000 | Kuslich | 606/61 |
| 6,059,790 A | 5/2000 | Sand et al. | 606/99 |
| 6,063,088 A | 5/2000 | Winslow | 606/61 |
| 6,080,155 A | 6/2000 | Michelson | 606/61 |
| 6,083,225 A | 7/2000 | Winslow et al. | 606/61 |
| 6,086,595 A | 7/2000 | Yonemura et al. | 606/99 |
| 6,096,038 A | 8/2000 | Michelson | 606/61 |
| 6,113,602 A | 9/2000 | Sand | 606/61 |
| 6,120,506 A | 9/2000 | Kohrs et al. | 606/80 |
| 6,123,705 A | 9/2000 | Michelson | 606/61 |
| 6,156,040 A | 12/2000 | Yonemura et al. | 606/99 |
| 6,159,214 A | 12/2000 | Michelson | 606/80 |
| 6,171,339 B1 | 1/2001 | Houfburg et al. | 623/17 |
| 6,174,311 B1 | 1/2001 | Branch et al. | |
| 6,210,412 B1 | 4/2001 | Michelson | 606/61 |

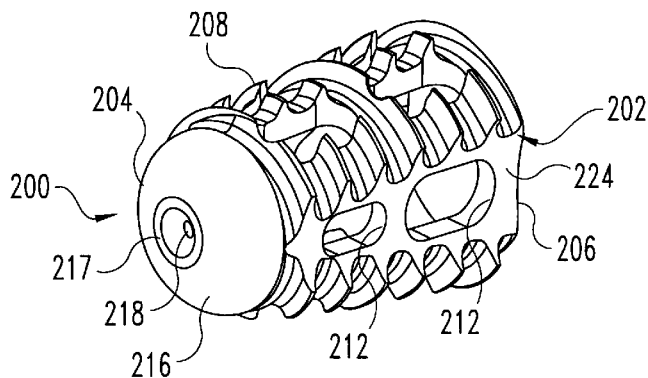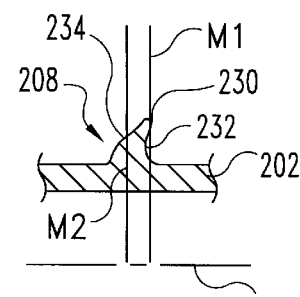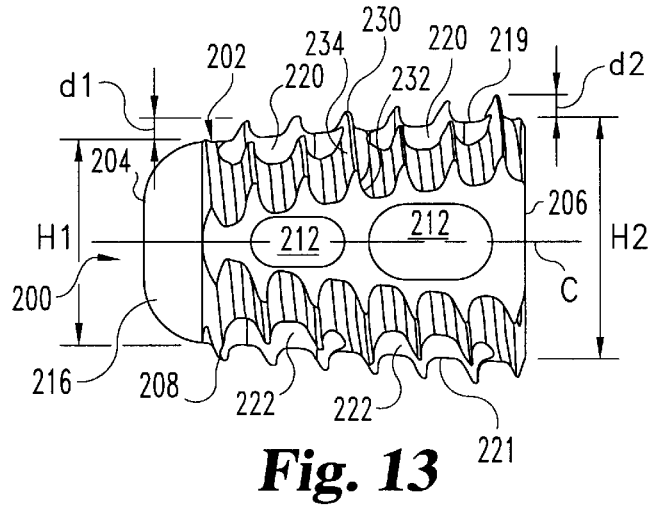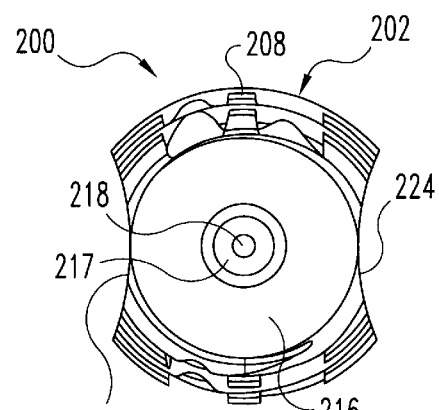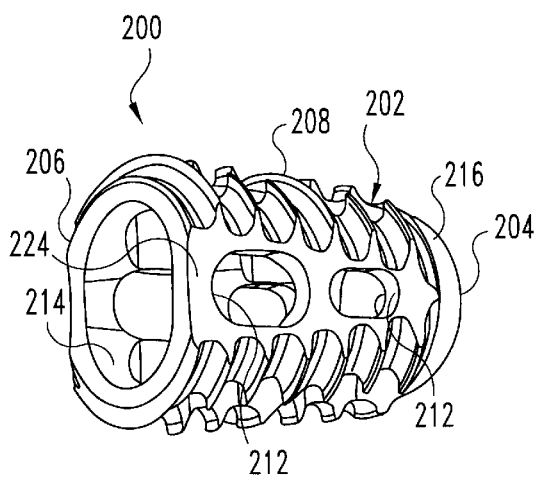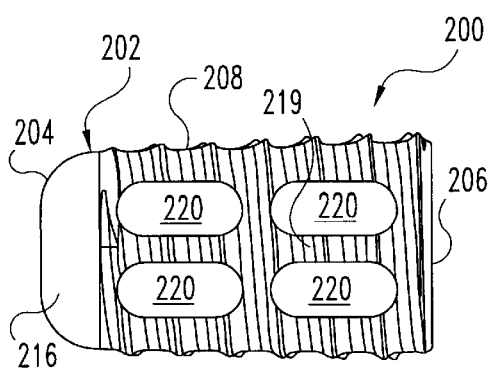

DEVICES AND METHODS FOR IMPLANTING FUSION CAGES

CROSS-REFERENCE TO RELATED APPLICATIONS

This application is a continuation application of pending U.S. patent application Ser. No. 09/649,696 filed on Aug. 28, 2000, which claims the benefit of the filing date of Provisional application Ser. No. 60/150,787, filed Aug. 26, 1999.

BACKGROUND OF THE INVENTION

The present invention relates generally to surgical procedures for spinal stabilization, and more specifically to instrumentation and techniques for inserting a spinal implant within the intervertebral disc space between adjacent vertebra. More particularly, while aspects of the present invention may have other applications, the invention provides instruments, techniques, and implants especially suited for implanting one or more fusion cages in an unreamed disc space.

There have been an extensive number of attempts to develop an exceptional intradiscal implant that could be used to maintain the height and stability of the disc interspace between adjacent vertebra, at least until complete arthrodesis is achieved. These "interbody fusion devices" have taken many forms. For example, one of the more prevalent designs takes the form of a cylindrical implant. These types of implants are presented in patents to Bagby, U.S. Pat. No. 4,501,269; Brantigan, U.S. Pat. No. 4,878,915; Ray, U.S. Pat. Nos. 4,961,740 and 5,055,104; and Michelson, U.S. Pat. No. 5,015,247. In the cylindrical implants, the exterior portion of the cylinder can be threaded to facilitate insertion of the interbody fusion device, as represented by the Ray, Brantigan and Michelson patents. In the alternative, some of the fusion implants are designed to be driven into the intradiscal space with little or no rotation. For example, this type of device is represented in the patent to Brantigan. A combination implant having the ability for threaded insertion or push-in insertion is disclosed in U.S. Pat. No. 5,782,919 to Zdeblick et al.

U.S. Pat. No. 5,484,437 to Michelson discloses a technique and associated instrumentation for inserting a fusion device. As described in more detail in the '437 patent, the surgical technique involves the use of a distractor having a penetrating portion that urges the vertebral bodies apart and a hollow sleeve having teeth at one end that are driven into the vertebrae adjacent the disc space created by the distractor. These teeth engage the vertebra to maintain the disc space height during subsequent steps of the procedure following removal of the distractor. In accordance with one aspect of the '437 patent, a drill is passed through the hollow sleeve to remove portions of the disc material and vertebral bone in order to ream the disc space and reduce the endplates to bleeding to produce a prepared bore for insertion of the fusion device. The drill is then removed from the sleeve and a fusion device having a diameter greater than the height of the disc space is positioned within the disc space using an insertion tool.

The device depicted in the Michelson patent is representative of this type of hollow implant which is typically filled with a bone growth inducing substance to promote bone growth into and through the device. This implant includes a plurality of circular apertures which communicate with the hollow interior of the implant, thereby providing a path for tissue growth between the vertebral end plates and the bone growth material within the implant.

One problem that is not adequately addressed by the above prior devices concerns restoring and maintaining the normal anatomy of the fused spinal segment. Naturally, once the disc is removed, the normal lordotic or kyphotic curvature of the spine may be altered. In response to this problem, the adjacent vertebral bodies may be reamed with a cylindrical reamer that fits the particular shape of the implant. In some cases, distraction techniques are used to establish the normal curvature prior to reaming. However, for a cylindrical implant, the over-reaming of the posterior portion is generally not well accepted because of the extensive removal of load bearing bone of the vertebrae. Over time, the implant tends to migrate into the vertebral bodies since the load-bearing surfaces of the endplates are no longer adequate for the implant to support the spinal column loads. This migration is often referred to as subsidence. When an implant subsides into adjacent bone, the disc space can collapse, resulting in potentially adverse consequences to the patient's health.

Another problem is that when the disc space and adjacent endplates are reamed, the implant must have a height greater than that of the original disc space height to restore the disc space to its normal anatomy. When large implants are bi-laterally inserted in the disc space, the lateral spacing and separation between the implants that can be attained is less than that attainable with smaller implants used in the same disc space. This positions the larger implants closer to the medial portion of the disc space and vertebral endplates, thus increasing the risk of migration into the vertebral bodies and subsidence of the spinal column around the implant. Also, lateral stability of the spinal column is reduced since less support is provided at the hardy bony peripheral ring of the adjacent vertebral bodies. Thus, it is desirable to maintain proper lateral separation of the implants in the disc space so that each implant is bearing on the strongest portion of the vertebral bodies and the lateral stability of the spinal column is maintained.

While the more recent techniques and instrumentation represent an advance over earlier surgical procedures for the preparation of the disc space and insertion of the fusion device, the need for improvement still remains. There remains a need for interbody fusion cages that may be inserted into an unreamed disc space, as well as instruments and techniques for inserting these fusion cages in an unreamed disc space to stabilize the spine. The present invention is directed to these needs and provides convenient methods, instruments, and implants for effective preparation of an unreamed disc space in conjunction with implant placement.

SUMMARY OF THE INVENTION

One object of the present invention is to provide instruments permitting placement of a fusion cage in an unreamed disc space. One instrument of the present invention includes a first distractor and a second distractor configured to be inserted in side-by-side relation in the disc space. At least one distractor has a guide surface abutting the other distractor to maintain the distractor spacing as the distractor pair is inserted into the disc space. In a preferred form, the guide surface is offset from the central axis of the instrument.

In one specific embodiment, each distractor has a body portion with a leading end and a trailing end. The body portions distract the disc space and form a channel therethrough as the distractors are inserted. Preferably, at least one of the distractors is provided with a medially extending portion extending from the body portion towards medial area of the disc space. The guide surface is formed by a medial side of the medially extending portion. The medially extending portion can be provided with a height less than that of the body portion. The guide surface of the medially extending portion guides the insertion of a cage into the distraction channel formed through the unreamed disc space remaining after withdrawal of the other distractor.

In another instrument of the present invention, first and second distractors are provided with first and second central spacers. Each central spacer has a width between its guide surface and the body portion of the distractor from which it extends. The central spacers extend medially from the body portion into the disc space so that the guide surfaces are adjacent one another. In one form, the first central spacer has a width that is greater than the width of the second central spacer. The guide surfaces maintain the spacing between the body portions as the first and second distractors are inserted into the disc space. Alternatively, the central spacers are provided with an equal width. In another form, the first and second distractors each further include a lateral spacer having a width that tapers from a maximum width at the trailing end of the body portion to a minimum width at the distal end of the body portion. It is preferred that the body portion have a diameter that is substantially the same as the diameter of the leading end of the fusion cage to be inserted into the disc space. In one preferred form, the guide surface of the central spacer of the first distractor guides the insertion of an implant into the distraction channel formed through the unreamed disc space remaining after withdrawal of the second distractor.

In yet another specific embodiment of the distractors of the present invention, the leading end of the body portion is tapered to facilitate insertion of the distractor into the unreamed disc space. Alternatively, the leading end of the body portion is rounded. It is also contemplated that the top and/or bottom surfaces of the body portion contacting the vertebral endplates may be roughened along a portion of the length of the body portion starting at the trailing end. The roughened surface scrapes the vertebral endplate during insertion and resists migration of the distractors in the disc space. The body portions of the distractors can also include a hollow threaded cylindrical hole or bore to connect the distractor to an obturator or shaft used for inserting and withdrawing the distractors.

In another aspect of the present invention, a method of distracting a disc space is provided. The method comprises providing a first distractor having a first longitudinal axis and a guide surface spaced a first distance from the first axis, and providing a second distractor having a second longitudinal axis. Each distractor is connected with a corresponding shaft, and positioned with the guide surface abutting a side of the second distractor. The first and second distractors are simultaneously inserted to distract the disc space to form a distraction channel.

In one form, the method additionally includes preparing a starter channel at the anterior lip of the disc space adjacent the first distractor. A channel starter instrument is provided with an outer shaft and an inner shaft. A cutting blade is positioned between the outer shaft and the inner shaft. The inner shaft has an end portion received within an opening formed at the trailing end of the first distractor. The cutting blade removes a portion of the endplate thickness at the anterior lip of the vertebral bodies, thus forming a starting channel in the disc space that is coextensive with the channel formed in the disc space by the removed second distractor. The above steps are repeated at the location of the first removed distractor if desired to form a second starter channel.

Yet a further aspect of the present invention provides a method for inserting one or more fusion cages in an unreamed disc space after insertion of the distractors as described above. The second distractor is removed from the disc space, forming a distraction channel in the disc space. A fusion cage, preferably having a root diameter or height approximating the disc space height, is inserted in the disc space. The first distractor guide surface maintains lateral positioning of the cage in the disc space as it is inserted. The first distractor is removed, and a spacer device is secured to the first fusion cage to act as a guide for insertion of a second fusion cage in the distraction channel formed by the first distractor.

In another form, the first and second fusion cages have openings in their top and bottom surfaces adjacent the endplates. A curette or other cutting instrument is placed into the cage, and the bone portion of the vertebral endplates adjacent the openings is removed. The remaining portion of the endplates in contact with the top and bottom surfaces of the cages remains intact to provide a strong bearing surface. Bone growth material is then placed within the fusion cages.

Yet another aspect of the present invention is to provide a fusion cage for insertion in an unreamed disc space. The cage includes a body having a hollow interior extending between a trailing end and a leading end. In one form, the body is threaded and tapered to restore lordosis when inserted in the disc space. The cage has a top surface and a bottom surface positioned in contact with the intact endplates of the vertebrae when the cage is implanted. The body defines a number of openings in the top and bottom surface. Preferably, external threads extend outwardly from the body portion and engage the cage to the bony end plates and harvest disc material and bone from the endplates for deposit through the openings into the hollow interior. In another form, the fusion cage is provided with threads with a swept back profile that increase in depth from the leading end to the trailing end to prevent backout of the inserted cage from the disc space.

One aspect of the invention contemplates providing an interbody fusion cage or device having opposed upper and lower bearing surfaces separated by a height. In one form, the height tapers along the length of the device to match angulation between endplates of adjacent vertebra. In a preferred form, the device includes migration resistance structures intended to limit movement of the fusion device in the disc space. Preferably, these migration resistance structures may include threads, ridges, knurling, spikes, or other surface irregularities extending from the bearing surface. One improvement of interbody fusion devices according to the present invention can be characterized as the spacing distance being substantially equal to the distance between unreamed endplates of adjacent vertebra thereby eliminating the need for removing vertebral endplate bone to form an insertion channel.

In another aspect of the invention, there is provided a method for preparing vertebral endplates through a fusion cage inserted in a disc space. The fusion cage includes at least one opening communicating with the endplate. Bone is removed from the endplate through the at least one opening after insertion of the fusion cage into the disc space.

In one preferred form, the fusion cage is inserted into a disc space having intact endplates. In another preferred form, a cutting instrument is provided that is inserted through the cage and configured to remove endplate bone material through the at least one opening. In one form, the cutting instrument includes a burr for removing bony material. In another form, the cutting instrument includes a curette for removing bony material. In yet another form, the cutting instrument is configured to remove bony material simultaneously from laterally adjacent holes through the fusion cage. In another preferred form, the fusion cage includes a guide at the trailing end of the cage opposite the at least one hole for the maintaining the cutting instrument alignment and facilitating use of the cutting instrument in the fusion cage.

Still a further object of the present invention is to provide a spinal disc space distractor assembly. The distractor assembly has a central axis extending therethrough. Preferably, the assembly includes a pair of distractors positioned in side-by-side relation, the distractors forming a guide surface therebetween. Preferably, the guide surface is offset a distance from the central axis.

The present invention also contemplates a method of preparing a disc space and inserting an implant in an unreamed disc space. The method utilizes one or more of the instruments and implants described above to prepare the disc space for receiving an implant.

Related aspects, features, forms, embodiments, objects and advantages of the present invention will be apparent from the following description.

BRIEF DESCRIPTION OF THE DRAWINGS

FIG. 13 is a side elevational view of a fusion cage according to another aspect of the present invention.

FIG. 13a is an enlarged cross-sectional view of a portion of the thread of the cage of FIG. 13.

FIG. 14 is a perspective view from the leading end of the fusion cage of FIG. 13.

FIG. 15 is an end elevational view of the trailing end of the fusion cage of FIG. 13.

FIG. 16 is a perspective view from the trailing end of the fusion cage of FIG. 13.

FIG. 17 is a top plan view of the fusion cage of FIG. 13.

DESCRIPTION OF THE ILLUSTRATED EMBODIMENTS

Figure 1:
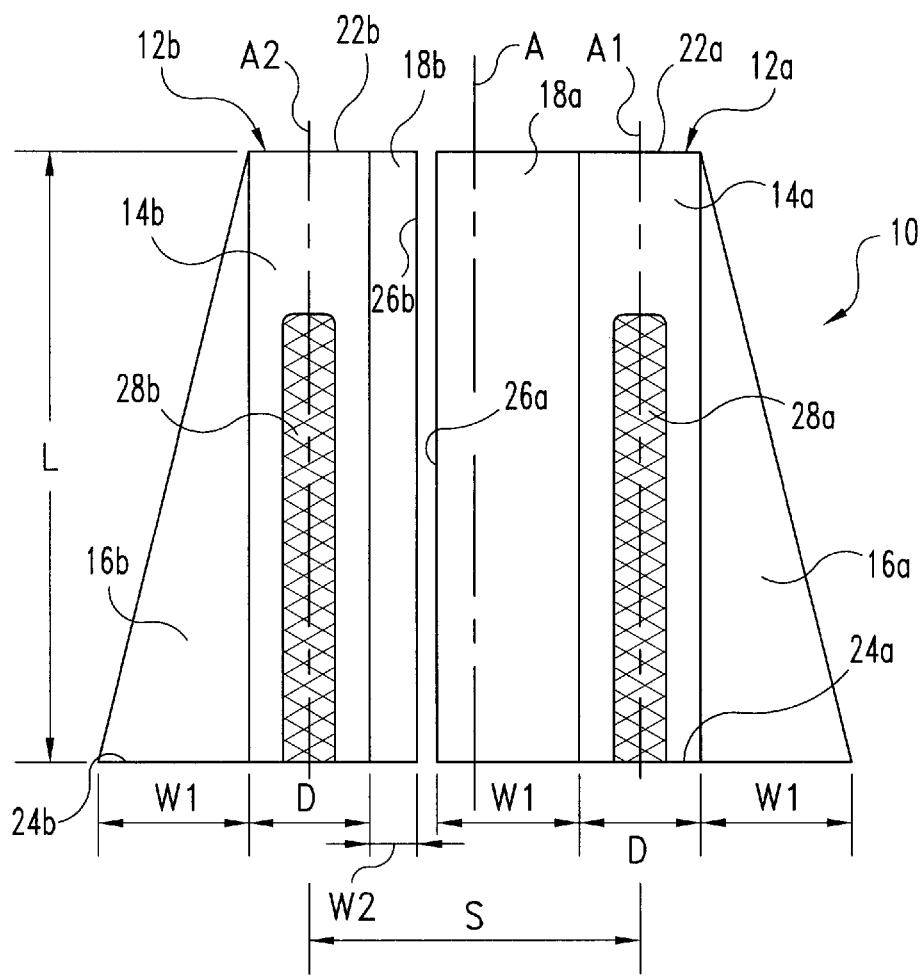
FIG. 1 is a top plan view of a distractor assembly according to one aspect of the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and any such further applications of the principles of the invention as illustrated therein are contemplated as would normally occur to one skilled in the art to which the invention relates.

The present invention relates generally to instruments, devices, and methods for performing vertebral interbody fusion. While it should be understood that the instruments and devices disclosed herein have many uses, it is particularly contemplated that they may be used to perform vertebral interbody fusion in an unreamed disc space with the endplates remaining completely or substantially intact. It is also particularly contemplated that the methods and instruments may be used in "open" or non-laparoscopic procedures. It is also contemplated that such procedures may be completed without requiring the use of cannulas or guide tubes, and that cages may be placed in the disc space using freehand techniques and other instruments known in the art. However, the instruments, methods and devices may be used and adapted if necessary, as known in the art, for use with guide tubes and laparoscopic procedures.

Figure 2:
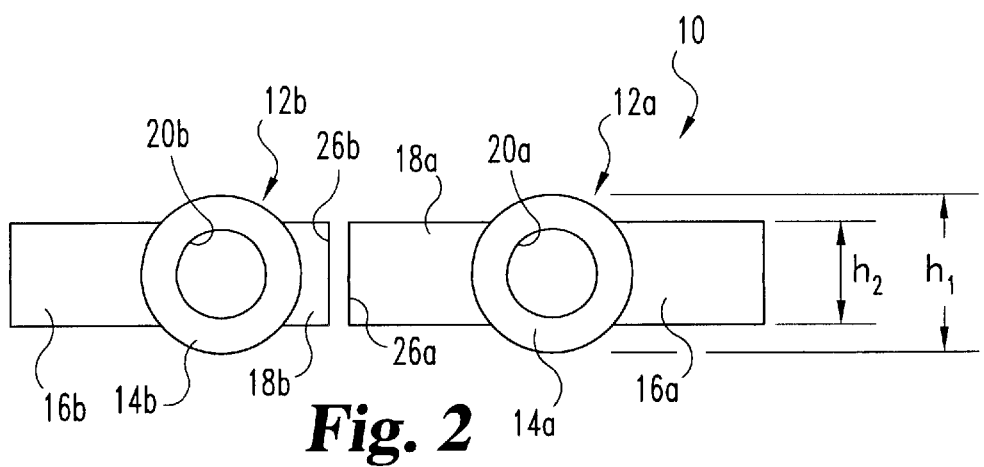
FIG. 2 is an end view of the distractor assembly of FIG. 1.

Referring now to FIGS. 1–2, there is shown a distractor assembly according to one aspect of the present invention. Distractor assembly 10 may be coupled to one or more obturators or shaft assemblies, as described in detail below with respect to FIG. 3, for insertion of distractors 12a and 12b into a disc space between the endplates of adjacent vertebra in order to restore the proper disc space height prior to insertion of a fusion cage or other implant therein. Distractor assembly 10 has a central axis A and includes a first distractor 12a and a second distractor 12b positioned adjacent first distractor 12a. Distractors 12a and 12b have central axes A1 and A2 separated by a lateral spacing S.

Distractor 12a includes a body portion 14a around axis A1. Body portion 14a extends between a leading end 22a and a trailing end 24a, and preferably defines hollow opening 20a at trailing end 24a. Extending laterally from body portion 14a is lateral spacer 16a, and extending medially from body portion 14a is central spacer 18a. Central spacer 18a defines a guide surface 26a adjacent second distractor 12b. Second distractor 12b includes a body portion 14b around axis A2, and preferably defines hollow opening 20b at trailing end 24b. Body portion 14b extends between a leading end 22b and a trailing end 24b. Extending laterally from body portion 14b is lateral spacer 16b, and extending medially from body portion 14b is central spacer 18b. Central spacer 18b defines a guide surface 26b adjacent to and coextensive with guide surface 26a of first distractor 12a. It is contemplated that guide surfaces 26a and 26b abut one another when distractor assembly 10 is inserted into the disc space, but have been illustrated as slightly offset in FIGS. 1–2 for the purposes of clarity. The components of first and second distractors 12a and 12b may be recited herein collectively by referring to, for example, body portion 14 or lateral spacer 16.

Figure 3:
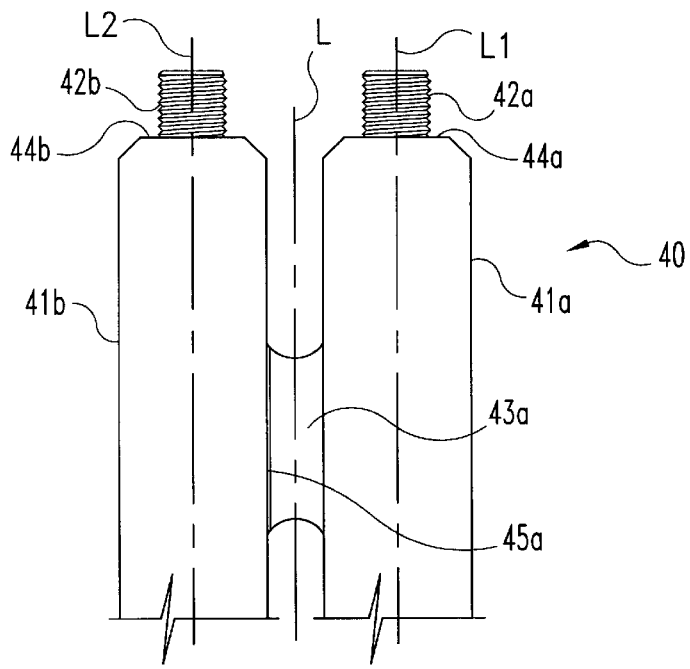
FIG. 3 is a partial top plan view of a shaft assembly connectable to the distractor assembly of the present invention.

It is further contemplated that a shaft assembly such as that shown in FIG. 3 may be provided with distractor assembly 10. Shaft assembly 40 that includes obturators or shafts 41a and 41b. Shaft 41a defines axis L1 and includes a threaded portion 42a to connect to a the shaft to a distractor. A shoulder 44a is configured to abut against trailing end 24a when distractor 12a is connected to shaft 41a with axes A1 and L1 coextensive. Threaded portion 42a is preferably threaded, and mates with corresponding threads formed in opening 20a. Shaft 41a also includes a cam 43a having a cam surface 45a along shaft 41b. Shaft 41b defines an axis L2 and includes a threaded portion 42b. A shoulder 44b is configured to abut against trailing end 24b when distractor 12b is connected to shaft 41b with axes A2 and L2 coextensive. Whiles portions 42b are preferably threaded, it is understood that any means known to those skilled in the art may be employed to connect the shaft to its corresponding distractor, and that the shafts need not be removable.

To insert the distractors 12a and 12b in the disc space, each distractor 12a and 12b is connected with the corresponding connecting portion 42a and 42b. Cam 43a maintains the lateral separation and relative alignment of shafts 41a and 41b as shaft 41b abuts against cam surface 45a. In an alternate embodiment, shaft 41a does not include cam 43a, but the shaft 41a has a lateral dimension sized to maintain contact and alignment between shafts 41a and 41b. The distractors 12a and 12b are simultaneously driven into the disc space and positioned using an impactor cap and hammering techniques applied to the proximal end of the shafts 41a and 41b as is know in the art. Lateral spacers 16 guide the distractor assembly 10 into the center of the disc space to ensure the distractor assembly 10 is in the proper location.

In one preferred embodiment, the distractor 12 has a knurled or roughened surface 28 on the top and on the bottom of body portion 14 adjacent the vertebral endplates. For ease of insertion, it is preferred that the surface of body portion 14 be substantially smooth adjacent leading end 22 and that roughened surface 28 not extend to leading end 22. In one specific embodiment, this smooth surface extends about 10 millimeters from leading end 22 towards trailing end 24. Knurled or roughened surface 28 can be made by teeth or any combination or pattern of indentations and projections formed on the surface of body 14. Each roughened surface 28 scrapes or removes a portion of bone material from the adjacent endplate of the vertebra as distractor assembly 10 is inserted into the disc space. Surfaces 28 help retain the distractor 12 in its inserted position during cage insertion. The roughened endplates facilitate bone growth by providing greater surface area for contact between the cage and the endplates, and also between the endplates and bone growth material placed within the cage.

Body portion 14 of each distractor has a lateral dimension D and a height h1. It is preferred that body portion 14 be cylindrical in shape, and thus D is the same as h1 and constant between leading end 22 and trailing end 24. However, other dimensions for D are also contemplated herein such that body portion 14 has other cross-sections, such as square, rectangular, ovoid, and elliptical, to name a few. In any event, height h1 corresponds to the height of the cage to be inserted in the disc space. Lateral spacers 16 have a width w1 extending from body portion 14 at trailing end 24. The width of lateral spacer tapers to converge with body portion 14 at leading end 22. It is also contemplated in an alternate embodiment that lateral spacers 16 have a width at leading end 22 that is less than the w1. Central spacer 18a has a width w1 extending from body portion 14a to guide surface 26a. Width w1 is preferably the same as the width of the lateral spacer 16a at trailing end 22a; however, a width w1 for central spacer 18a that differs from the width of lateral spacer 16a is also contemplated. Central spacer 18b has a width w2 extending from body portion 14b to guide surface 26b. Width w2 is preferably less than the width w1 of central spacer 18a. Central spacers 18 and lateral spacers 16 have a height h2 that is less than height h1 of body portion 14. It is preferred that height h2 be 4 to 6 millimeter less than height h1; however, other height differences are also contemplated.

The overall lateral dimension (w1+D+w2) of distractor 12b at its trailing end 24b preferably corresponds to the maximum cross-sectional dimension of the trailing end of the cage to be inserted. The leading end 22b has a width corresponding to the maximum lateral width of the leading end of the cage to be inserted. Also, shaft assembly 40 has shafts 40a and 40b, each having a width that corresponds to the overall lateral dimension (w1+D+w2) of distractor 12b. The cam 43a has a width sufficient to extend from shaft 41a to contact shaft 41b. In an alternate embodiment, it is contemplated that shaft 40a has a width that is equal to the width (w1+D+w1) of trailing end 24a of distractor 12a.

Figure 4:
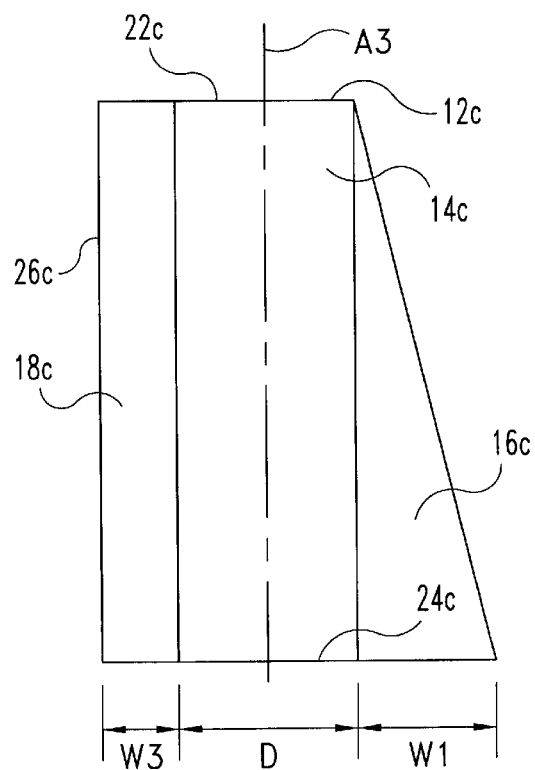
FIG. 4 is a top plan view of a third distractor usable with the distractor assembly of FIG. 1.

As shown in FIG. 1, longitudinal axes A1 and A2 of distractors 12a and 12b are separated by a lateral separation distance S, and each are offset a distance ½ S from central axis A of distractor assembly 10. It is most preferred that this separation distance maximizes the position of axes A1 and A2 in the disc space with respect the centerline of the spinal column. If it is desired or necessary to further increase separation distance S, a third distractor 12c, such as that shown in FIG. 4, may be used in place of distractor 12a. Distractor 12c is identical to distractor 12a, except that central spacer 18c has a width w3 that is greater than width w1 of distractor 12a. Use of distractor 12c thus increases the separation distance S between distractor axes L3 and L2 by an amount corresponding to the increase of width w3 over width w2. Alternatively, the surgeon may use a second distractor 12a in place of distractor 12b to increase the separation distance S by an amount corresponding to the increase of width w1 over w2.

It is further contemplated herein that distractor assembly 10 is modular, permitting interchangeability of various sized distractors 12 with the shaft assembly used therewith in order to increase the medial-lateral spacing of the distractors and the disc distraction height as needed. It is preferred that leading end 22 of the distractors 12 incorporate the identical geometry of the fusion cage to be implanted in the distracted disc space. For example, various distractors 12 could be provided with height h1 ranging from 9 millimeters to 17 millimeters in increments of 1 millimeter. The surgeon selects distractors 12 having a height h1 corresponding to the leading end of the cage to be inserted into the disc space. It is also contemplated that distractor assembly 10 can be used for final distraction of the disc space, i.e. as the last distractor inserted prior to insertion of the fusion cages or other implants into the disc space. Distraction of the disc space prior to insertion of distractor assembly 10 may be accomplished using any known distractor instrumentation and technique.

Figure 5A:
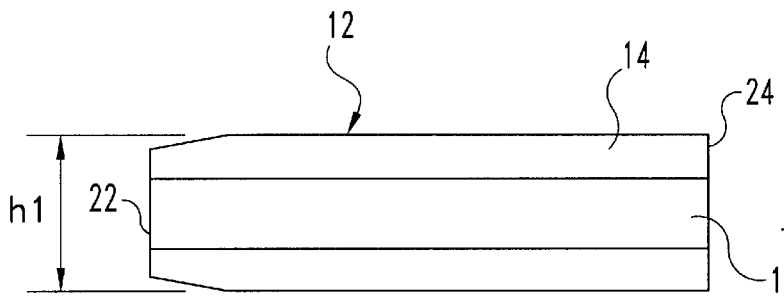
FIG. 5(a) is a side elevational view of a further embodiment of a distractor of the distractor assembly of FIG. 1.
Figure 5B:
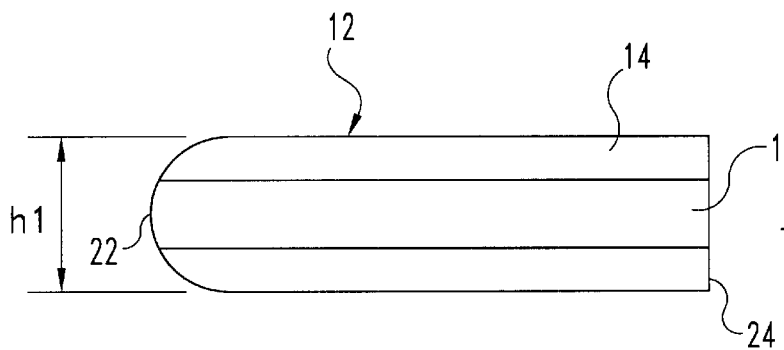
FIG. 5(b) is a side elevational view of another embodiment of a distractor of the distractor assembly of FIG. 1.
Figure 6:
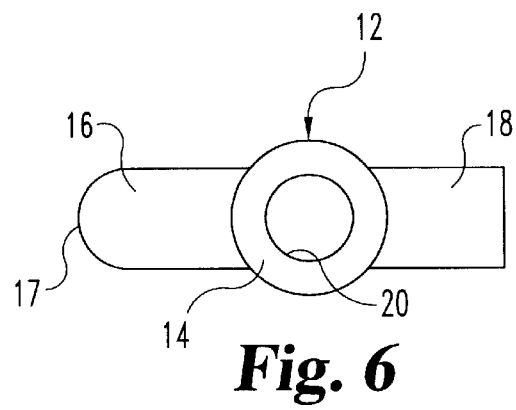
FIG. 6 is an end elevational view of yet a further embodiment of a distractor of the distractor assembly of FIG. 1.

Referring now to FIGS. 5(a) and 5(b), side elevational views of alternate embodiments for distractor 12 are shown. In FIG. 5(a), the distractor 12 has leading end 22 that is tapered to a height at leading end 22 that is less than h1. The tapered leading end facilitates insertion of the distractor 12 into the disc space. In FIG. 5(b), the leading end 22 is rounded to form a "blunt nose" at leading end 22. Other shapes and configurations for leading end 22 are also contemplated herein. In FIG. 6, lateral spacer 16 is shown with a rounded edge 17 that extends from leading end 22 to trailing end 24. Rounded edge 17 further facilitates and eases introduction of the distractor 12 into the disc space.

Figure 7:
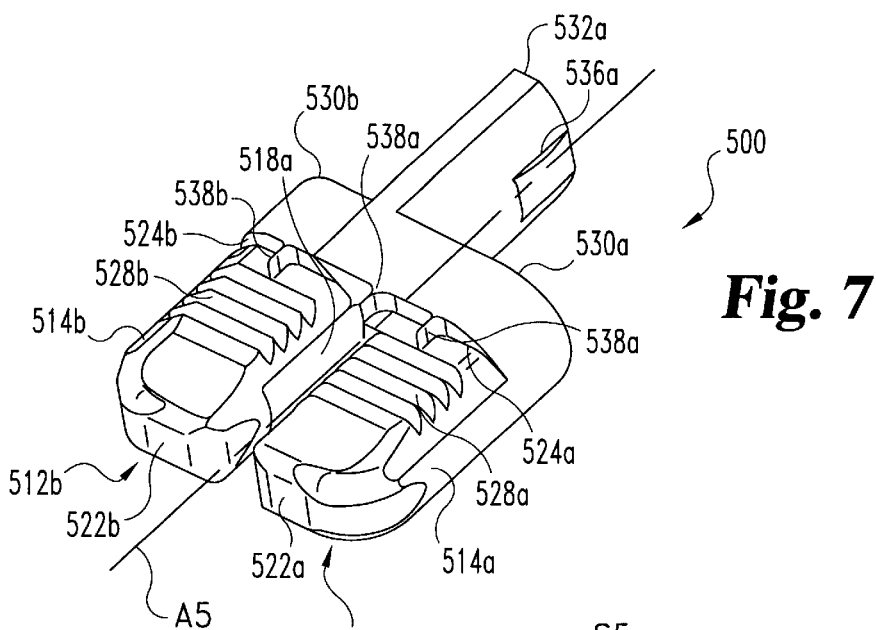
FIG. 7 is a perspective view of another embodiment distractor assembly according to the present invention.
Figure 8:
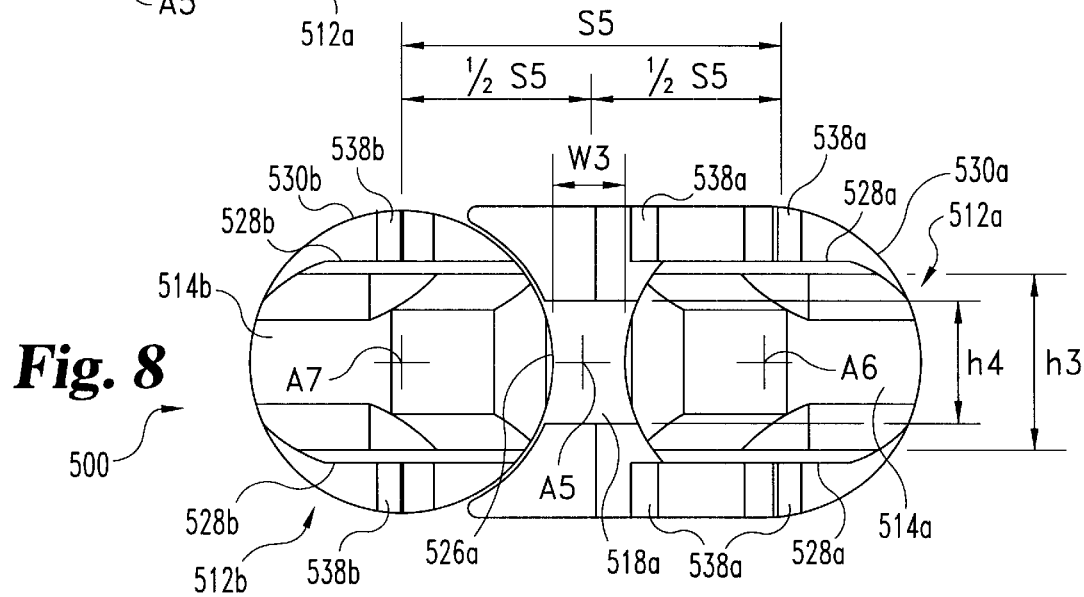
FIG. 8 is a left end elevational view of the distractor assembly of FIG. 7.
Figure 9:
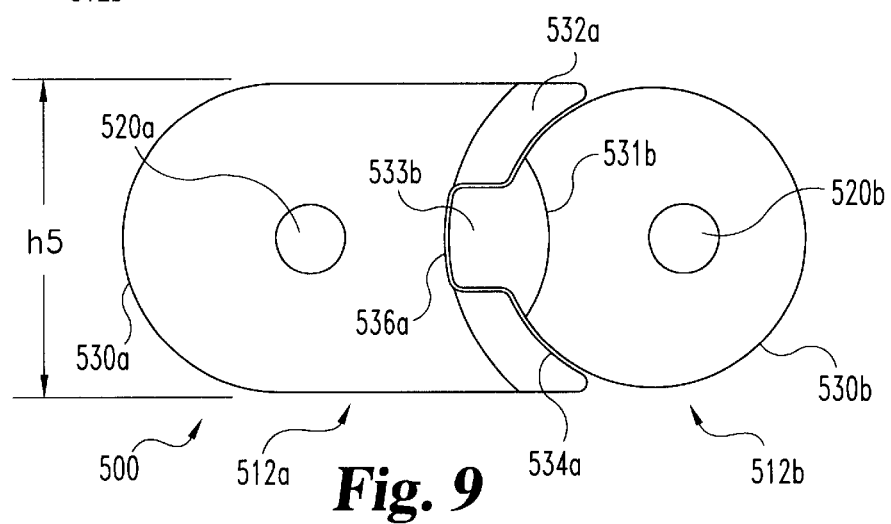
FIG. 9 is a right end elevational view of the distractor assembly of FIG. 7.

Referring now to FIGS. 7–9, there is shown a further embodiment of the distractor assembly according to the present invention. Distractor assembly 500 may be coupled to one or more obturators or shaft assemblies, as described above with respect to FIG. 3, for insertion of distractors 512a and 512b into a disc space between the endplates of adjacent vertebra in order to restore the proper disc space height prior to insertion of a fusion cage or other implant therein. Distractor assembly 500 has a central axis A5 and includes a first distractor 512a and a second distractor 512b positioned adjacent first distractor 512a. Distractors 512a and 512b have central axes A6 and A7 separated by a lateral spacing S5.

Distractor 512a includes a body portion 514a around axis A6. Body portion 514a extends between a leading end 522a and a trailing end 524a. Extending medially from body portion 514a is a central spacer or medial portion 518a. Medial portion 518a defines a guide surface 526a adjacent to and abutting body portion 514b of second distractor 512b. Formed with and extending proximally from trailing end 524a of body portion 514a is a connecting portion 530a for connecting distractor 512a to a shaft. Connecting portion 530a includes a guide arm 532a extending proximally therefrom. Guide arm 532a includes a medially facing guide surface 534a that is coplanar with and forms an extension of guide surface 526a of medial portion 518a. As described further below, a shaft of an implant insertion instrument is positionable against guide surface 534a during implant insertion to assist in maintaining the proper positioning and spacing of the cage during insertion along guide surface 518a. A notch 536a is formed in the proximal end of arm 532a.

Second distractor 512b includes a body portion 514b around a central axis A7. Body portion 514b extends between a leading end 522b and a trailing end 524b. Distractor 512b further includes a connecting portion 530b extending proximally from trailing end 524b of body portion 514b for connecting distractor 512b to a shaft. Connecting portion 530b includes a proximally extending extension arm 531b having a protrusion 533b extending medially therefrom towards first distractor 512a. Protrusion 533b is positionable in notch 536a to prevent distractors 512a and 512b from rotating relative to one another during insertion of distractor assembly 500 into the disc space. It is contemplated that side of body portion 514b abutting guide surface 526a is rounded convexly and that guide surface 526a is rounded concavely fit in close engagement with body portion 514b.

Connecting portions 530a and 531b each have a height h5 that is greater than the height h4 of its connect body portion 514a and 514b, respectively. Further, distractor 512a includes two anchoring members 538a extending from connecting portion 530a towards leading end 522a along the top surface of body portion 514a and two anchoring members 538a extending along the bottom surface of body portion 514a. Similarly, distractor 512b includes one anchoring member 538b extending from connecting portion 531b towards leading end 522b along the top surface of body portion 514b and one anchoring member 538b extending along the bottom surface of body portion 514b. It will be understood that more or fewer anchoring members 538a, 538b can be provided, and that anchoring members 538a, 538b may be provided only along the top surface or bottom surface of the distractor body portions 514a and 514b. Anchoring members 538a, 538b are preferably wedge shaped so as to engage into the cortical bone of the vertebral endplate as the distractor assembly 500 is driven into the disc space so as to resist lateral migration of distractor assembly 500 and distractors 512a, 512b during the surgical procedure.

Like components of first and second distractors 512a and 512b may be recited herein collectively by referring to, for example, body portion 514. A shaft assembly, such as that described above with respect to FIG. 3, may be provided with distractor assembly 500. As shown in FIG. 9, the proximal or trailing end wall of distractor 512a includes threaded opening 520a formed in connecting portion 530a and the proximal or trailing end wall of distractor 512b includes threaded opening 520b formed in connecting portion 531b. Threaded portion 42a of shaft 41a can be threaded into opening 520a and threaded portion 42b of shaft 41b can be threaded into opening 520b.

To insert the distractors 512a and 512b in the disc space, each distractor 512a and 512b is connected with the corresponding threaded portion 42a and 42b of shafts 41a and 41b, respectively. The proximal ends of the shafts 41a and 41b are secured by an impacting cap that holds the shafts together and distributes a driving force between distractor 512a and distractor 512b to simultaneously distractors 512a and 512b into the disc space.

In one preferred embodiment, each distractor 512 has a knurled or roughened surface in the form of teeth 528 on the top and on the bottom of body portion 514 adjacent the vertebral endplates. For ease of insertion, it is preferred that the surface of body portion 514 be substantially smooth and rounded adjacent leading end 522 and that teeth 528 not extend to leading end 522. It is also contemplated that leading end 522 of body portion 514 has a height h3 corresponding to the root diameter height of the leading end of the cage to be inserted. Teeth 528 can be made by any combination or pattern of indentations or recesses and projections formed on the top and bottom surfaces of body 514. Each tooth 528 can also be configured to scrape or remove a portion of bone material from the adjacent endplate of the vertebra as distractor assembly 500 is inserted into the disc space. Teeth 528 help retain distractor 512 in its inserted position during cage insertion. The roughened vertebral endplates facilitate bone growth by providing greater surface area for contact between the cage and the endplates, and also between the endplates and bone growth material placed within the cage.

Medial portion 518a has a width w1 extending from the medial most edge of body portion 514a to the portion of guide surface 526a closest to body portion 514a. Width w3 is sized to achieve the desired lateral spacing between the distractor 512a and 512b and subsequently the fusion cages that will be inserted into the disc space locations initially occupied by these distractors. For example, in one specific embodiment, medial portion 518a provides a spacing w3 of 2 millimeters. In another specific embodiment, medial portion 518a provides a spacing of 4 millimeters. Other spacing dimensions are also contemplated. Medial portion 518a has a height h4 that is less than height h3 of body portion 514a. It is preferred that height h4 be 4 to 6 millimeter less than height h3; however, other height differences are also contemplated. Medially extending portion 518a has a length extending from the trailing end of body portion 514a to a position proximate leading end 522a, and in the illustrated embodiment has a length about three-fourths the length of body portion 514a.

As shown in FIG. 8, longitudinal axes A6 and A7 of distractors 512a and 512b are separated by a lateral separation distance S5, and each are offset a distance ½ S5 from central axis A5 of distractor assembly 500. It is preferred that this separation distance maximizes the separation of axes A6 and A7 in the disc space with respect the centerline of the spinal column. Guide surface 526a is offset laterally from central axis towards second distractor 512b.

It is further contemplated herein that distractor assembly 500 is modular, permitting interchangeability of various sized distractors 512 with each other and with the shaft assembly used therewith in order to increase or decrease the medial-lateral spacing of the distractors and the disc distraction height as needed. It is preferred that leading end 522 of distractors 512 incorporate the identical geometry of the fusion cage to be implanted in the distracted disc space. For example, various distractors 512 could be provided with height h3 ranging from 9 millimeters to 17 millimeters in increments of 1 millimeter. The surgeon selects distractors 512 having a height h3 corresponding to the leading end of the cage to be inserted into the disc space. It is also contemplated that distractor assembly 500 can be used for final distraction of the disc space, i.e. as the last distractor inserted prior to insertion of the fusion cages or other implants into the disc space. If necessary, distraction of the disc space prior to insertion of distractor assembly 500 may be accomplished using any known distractor instrumentation and technique.

After insertion of distractor assembly 500 in the disc space with leading ends 522a and 522b at the proper depth distally in the disc space, and the distractor axes A6 and A7 at the desired lateral spacing S5, distractor 512b may be removed from the distracted disc space with distractor 512a remaining in its inserted position. The distraction channel formed in the disc space by removed distractor 512b acts as a guide for a first fusion cage to follow during insertion. Distractor 512a also acts as a guide for insertion of the first fusion cage into the portion of the disc space occupied by distractor 512b. The distraction channel and guide surface 526a of medial portion 518a maintain the lateral positioning of the first fusion cage with respect to axis A and distractor 512a, and also resists medial migration of the first cage in the disc space during its insertion. After the first cage is inserted, distractor 512a is removed and the first cage guides insertion and resists medial migration of the second cage as it is inserted into the disc space. It is preferred that the cages be threaded to resist backout from the disc space, and are also preferably tapered to restore spinal lordosis.

Figure 10:
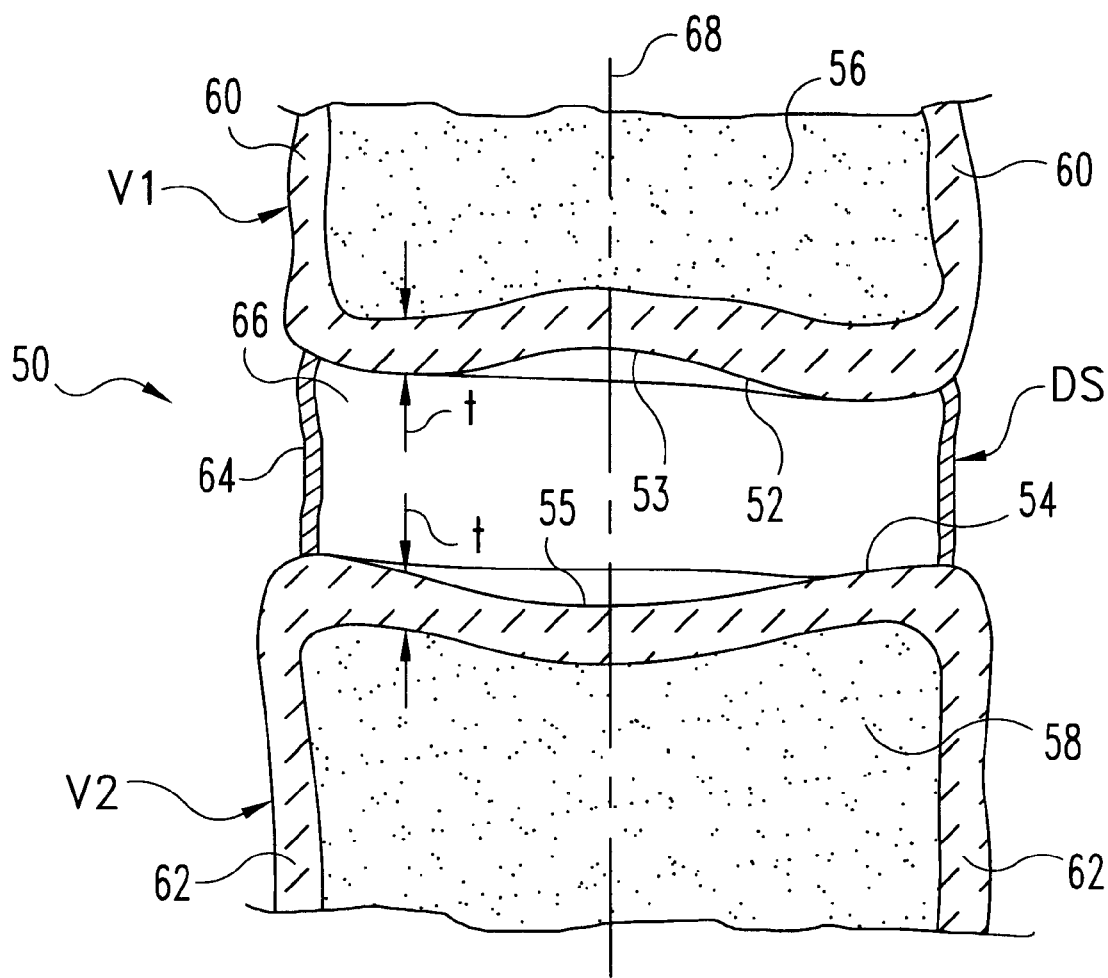
FIG. 10 is a partial sectional view taken along the spinal column of a segment of the spinal column.

Referring to FIG. 10, there is illustrated an example of a segment of the spinal column to which the present invention has application. Spinal column segment 50 includes adjacent vertebra V1 and V2 and disc space DS therebetween around a central axis 68. Annulus 64 surrounds disc space DS and extends between vertebra V1 and V2. Each vertebra V1, V2 includes a bony endplate 52, 54 and an outer peripheral ring 60, 62, surrounding a softer inner portion 56, 58, respectively. Endplates 52, 54 each have a thickness t and typically include concave areas 53 and 55, respectively. Endplates 52, 54 and peripheral rings 60, 62 are made from hard bony material, and provide the lateral stability and load distributing capabilities of a healthy spinal segment 50.

Figure 11:
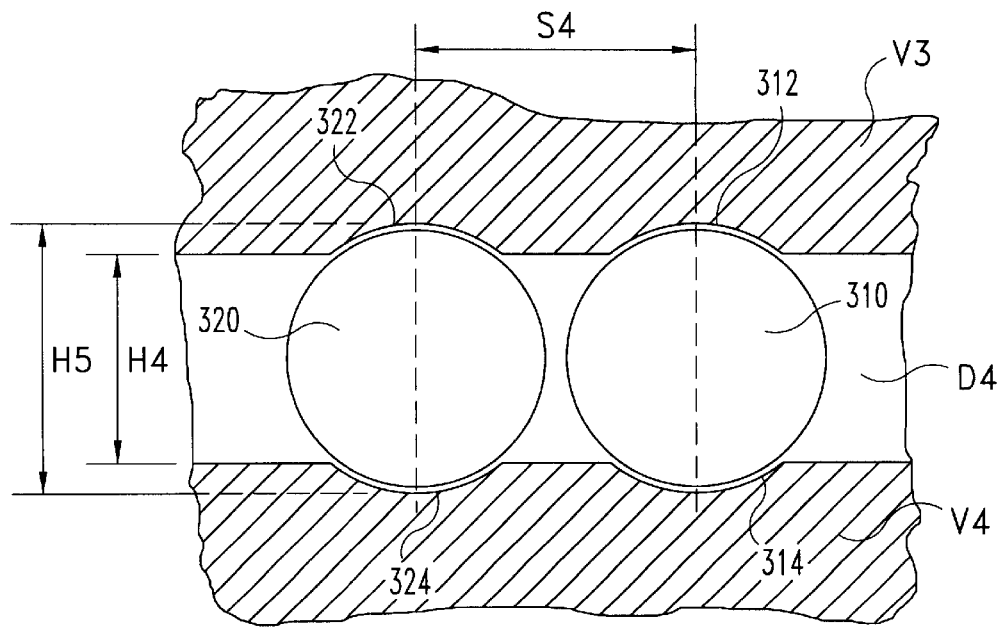
FIG. 11 is a partial cross-sectional end view illustrating prior art fusion devices inserted into a disc space.
Figure 12:
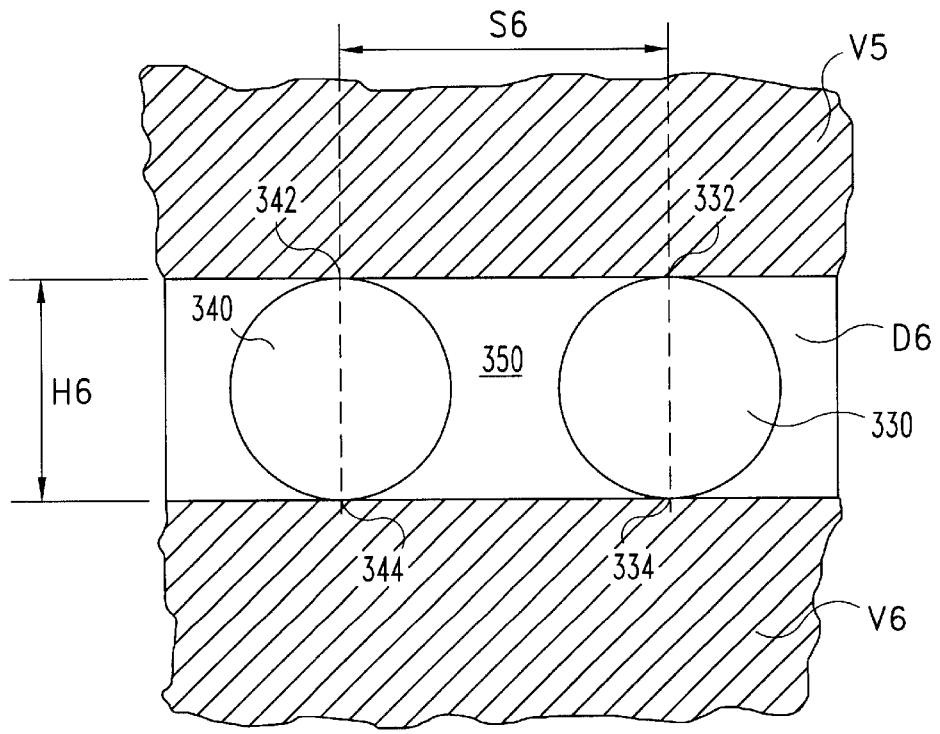
FIG. 12 is a partial cross-sectional end view illustrating fusion devices according to the present invention inserted into the disc space.
Figure 18:
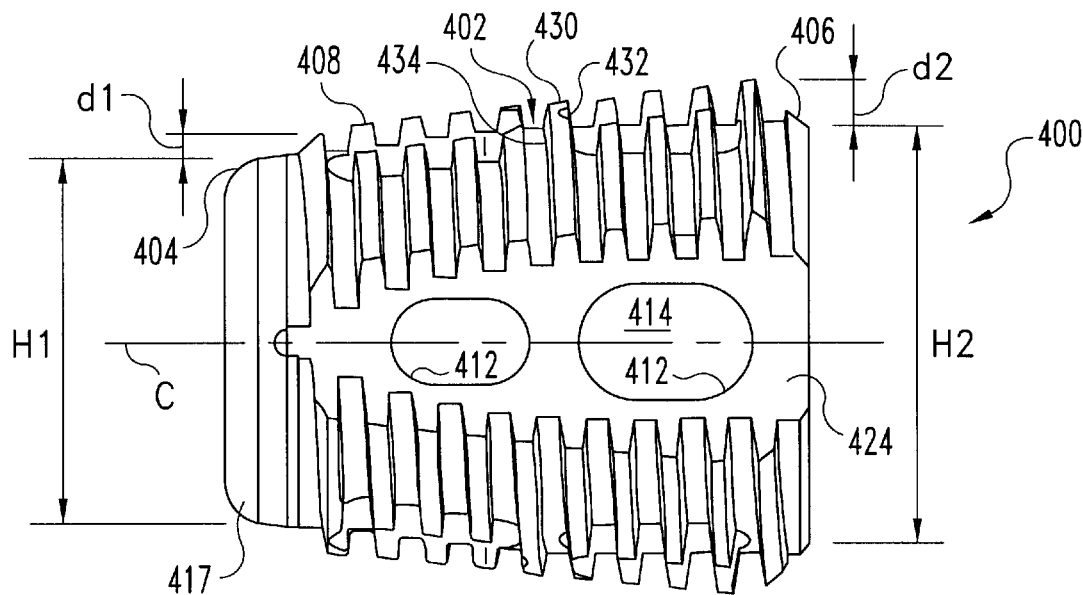
FIG. 18 is a side elevational view of a fusion cage according to another aspect of the present invention.
Figure 19:
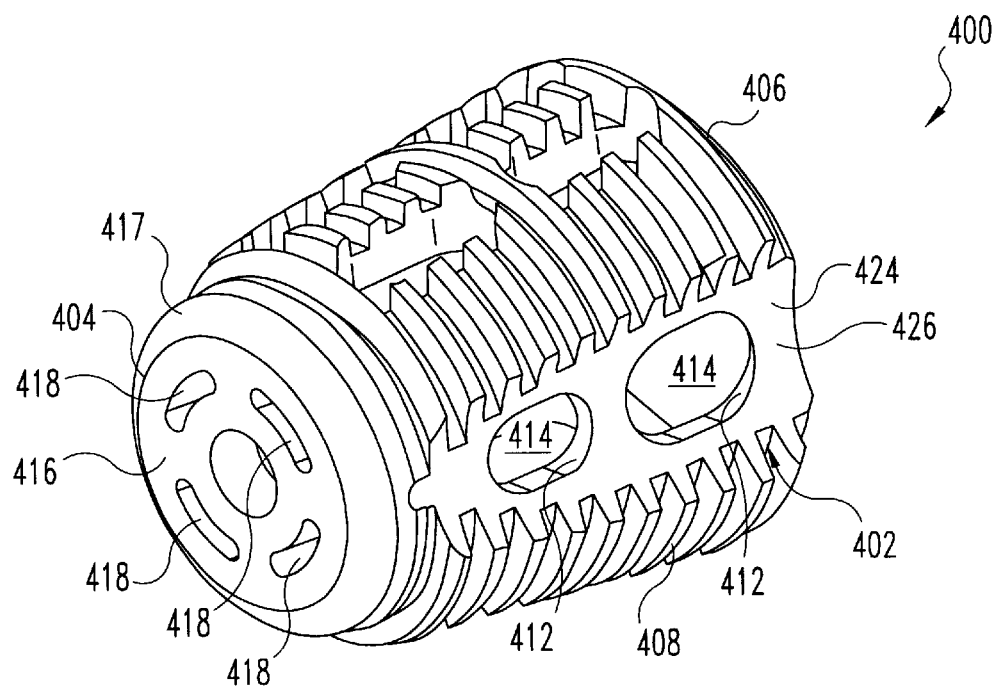
FIG. 19 is a perspective view from the leading end of the fusion cage of FIG. 18.
Figure 20:
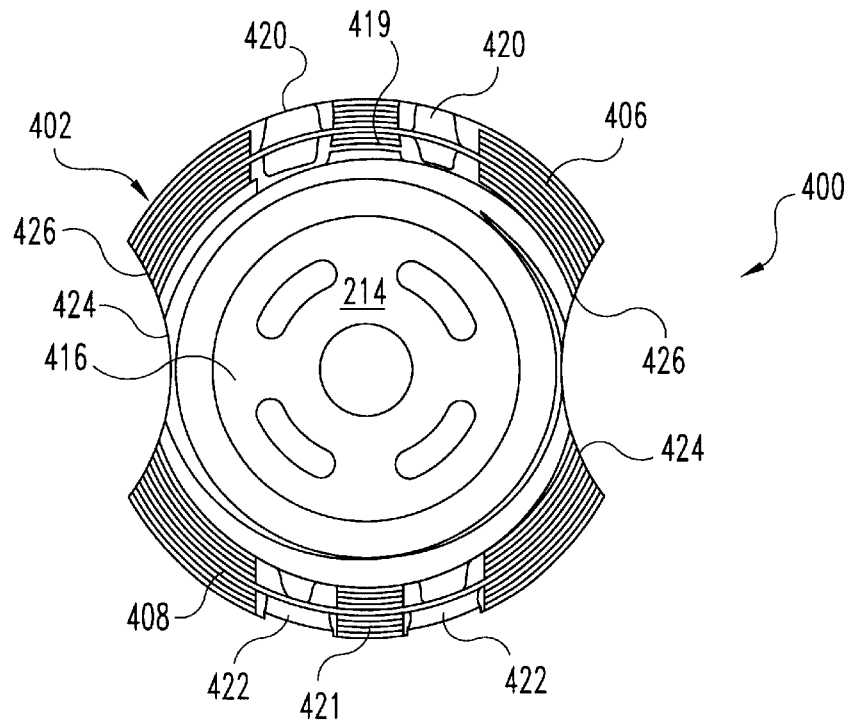
FIG. 20 is an end elevational view of the trailing end of the fusion cage of FIG. 18.

Distractors 12a, 12b and 512a, 512b may each form a channel at a desired lateral location in an unreamed disc space for the cage to follow during insertion. Distractor assembly 10 and 500 are particularly useful to provide and maintain the desired lateral positioning of the cages with respect to central axis 68 within an unreamed the disc space DS so each cage may be implanted in the desired position while preserving the thickness t of bony endplates 52, 54. Distractor assembly 10 and 500 also increases the lateral spacing between fusion cages with respect to axis 68 to increase load distribution to peripheral rings 60, 62 and increase the lateral stability of the spinal column segment. This increase in lateral spacing is illustrated in FIGS. 11 and 12. FIG. 11 shows a partial cross-sectional view of two prior art interbody fusion cages 310 and 320 placed in a disc space D4 disposed between adjacent vertebral bodies V3 and V4. As used herein, the term cage is intended to encompass any prior art fusion device or implant. Disc space D4 has a height H4. The fusion cages 310 and 320 have a height H5. The height H5 of the fusion cages is greater, typically by 4 to 6 mm, than the height H4 of the disc space. Thus, openings 312, 314, 322, and 324 must be formed in the vertebra to accommodate the extra height of the implants. These openings through the stronger bone of the endplates tend to weaken the bony area adjacent the implants, increasing the risk of implant subsidence. Further, the increased size of the implants requires them to be placed close together to avoid extending beyond the lateral edges of the disc space. The spacing between the centerline of cages 310 and 320 is distance S4.

Referring to FIG. 12, the present invention provides improved interbody fusion devices. Disc space D6 is disposed between vertebrae V5 and V6, and has a height H6. For purposes of illustration, height H6 is substantially identical to height H4 of FIG. 24. Thus, cages of the present invention, represented by cages 330 and 340, are positioned in disc space D6 with the endplates of vertebrae V5 and V6 substantially intact and supported by cages 330 and 340. The intact cortical bone decreases the risk of subsidence of cages 330 and 340 into the vertebrae V5 and V6. Cages 330 and 340 have substantially the same lateral spacing from the sides of the disc space as prior art cages 310 and 320 of FIG. 11. However, the centerline spacing S6 is substantially greater than centerline spacing S4. Thus, a void 350 is created that may be filled with a greater volume of bone in-growth material than possible with the prior art cages of FIG. 11. Further, the endplate contacts 332, 334, 342, and 344 are spaced farther apart thereby increasing the stability of the construct and subsequent fusion.

In accordance with this aspect of the invention, there is provided a fusion cage 200 as shown in FIGS. 13–17. Fusion cage 200 is particularly suited for insertion into an unreamed disc space in either the lumbar or cervical regions of the spine. Cage 200 eliminates the need for a channel discectomy and/or reaming of the disc space prior to insertion of the cage 200. Fusion cage 200 does not require a cannula, guide tube, or laparoscopic instrument for insertion into the disc space, although the use of such instruments and techniques associated therewith are not precluded by cage 200. It is also contemplated that the fusion cage 200 may be inserted using the techniques and instruments described herein. However, other known techniques and instruments may also be used to insert these cages.

Cage 200 includes body 202 extending between leading end 204 and trailing end 206. A number of threads or single thread 208 extend around body 202 between leading end 204 and trailing end 206 transverse to a central axis C. Body 202 defines a number of side apertures 212 in sidewalls 224 that communicate with a hollow interior 214. Cage 200 has a top bearing surface 219 that is adjacent the superior vertebral endplate when cage 200 is inserted. At top bearing surface 219 body 202 defines a number of top apertures 220. In a preferred embodiment, there are provided four top apertures 220 that are substantially the same size and symmetrically positioned about axis C. A bottom bearing surface 221 includes a number of bottom apertures 222 corresponding in size, shape and location to top apertures 220. It is desirable that hollow interior 214 be filled with BMP material, bone graft, chips or other bone growth compound to effect fusion between the vertebrae.

An end cap or end nose 216 is provided at leading end 204 and formed with body 202. End nose 216 has a recess 217 formed therein along a center axis of cage 200. End nose 216 further includes an opening 218 formed therethrough at the center of recess 217 that communicates with interior 214 to provide a path for blood flow through leading end 204 of cage 200, further increasing the porosity of cage 200 for fusion. Recess 217 allows opening 218 to be offset proximally or towards trailing end 206 in relation to the distalmost end of leading end 204. This protects the tissue in the disc space from contact with sharp or abrupt edges that might be formed around hole 218. End nose 216 preferably has a rounded configuration between the top and bottom bearing surfaces that matches the profile of the distractor used to distract the disc space. This allows end nose 216 to also distract the disc space, if necessary, as cage 200 is threaded into the disc space. Preferably, end nose 216 is unthreaded and has a length along axis C that corresponds to about 15% of the overall length of cage 200 between leading end 204 and trailing end 206.

For ease of insertion and maintenance of position in the disc space, it is contemplated that body 202 includes one or more threads 208 along at least a portion of the length of body 202 that are self-tapping. Preferably, threads 208 are spaced sufficiently such that body 202 can contact the vertebral endplates between adjacent ones of the threads. In one specific embodiment, thread 208 has a pitch of 3 so that cage 200 advances 3 mm into the disc upon a complete revolution of cage 200 about axis C. It is also contemplated that the threads gradually increase in depth from d1 to d2 as threads 208 run from leading end 204 to trailing end 206. In one specific embodiment, it is contemplated that depth d1 will correspond to about 1.0 mm and depth d2 will correspond to about 1.5 mm.

The form of threads 208 facilitate the cutting of threads 208 into the cortical bone of the intact vertebral endplates in the unreamed disc space. As shown in further detail in FIG. 13a, thread 208 includes a sharp crest 230 that may be slightly truncated, a concave trailing wall 232 extending from crest 230 to body 202, and a convex leading wall 234 extending from crest 230 to body 202. Sharp crest 230 cuts into the cortical bone and advance cage 200 as it is threaded into the disc space. Such a configuration prevents the adjacent vertebral bodies from riding up on threads 208, thereby preventing the disc space height from increasing substantially above body 202 of cage 200 as it is threaded into position. The cortical bony endplates are thus maintained in substantial contact with body 202 between threads 208, and threads 208 are embedded into the cortical bone of the endplates. Undesirable subsidence of the vertebrae along threads 208 is avoided, and threads 208 secure cage 200 to the cortical bone of the vertebral endplates rather than the cancellous bone. Subsidence is also resisted by body 202 of cage 200 body 202 supports the hard cortical bone of the adjacent vertebral endplates. Resistance to expulsion of cage 200 from the disc space is also increased since thread 208 achieves greater purchase into the cortical bone.

As cage 200 is threaded into the disc space, the material harvested by thread 208 is scaved and deposited through openings 220 and 222 and into hollow interior 214. This depositing of material is enhanced by the configuration of thread 208. As shown in FIG. 13a, crest 230 has a vertically oriented midline M1 perpendicular to central axis C of cage 200. The base of thread 208 has a second midline M2 perpendicular to central axis C. Midline M2 is distally offset from midline M1 towards leading end 204. This swept back profile of thread 208 and concave trailing wall 232 assist in depositing bony material into openings 220 and 222 as cage 200 is threaded into the disc space.

Body 202 is tapered along its length from height H1 at leading end 204 to height H2 at trailing end 206 to define an angle that restores the natural curvature of the spine when inserted into the disc space. The tapered body 202 further distracts the proximal portion of the disc space in accordance with the increase in height associated with the taper of body 202 as cage 200 is threaded into the disc space. As cage 200 is inserted, threads 208 achieve purchase into the intact cortical bone of the adjacent vertebral endplates. The increase in thread depth from leading end 204 to trailing end 206 provides greater purchase of the portion of thread 208 adjacent trailing end 206 into the bony endplate, and, along with the swept back profile of thread 208, reduces the risk of cage 200 backing out or un-threading from the disc space. Thus, maintenance of cervical and lumbar lordosis is improved and the risk of subsidence associated with implants inserted into a reamed disc space is eliminated.

Other advantages realized by cage 200 are associated with its relatively smaller size as compared to cages inserted in reamed openings. Since the endplates of the vertebrae are not reamed, the overall heights H1 and H2 of cage 200 are less than that required for a cage inserted into a reamed disc space. Typically, heights H1 and H2 will be about 4 to 6 millimeters less than the corresponding heights of a cage for a reamed disc space. Also, the concave sidewalls 224 of cage 200 reduce the lateral dimension of the inserted cage 200. Thus, if two cages 200 are bilaterally inserted into the disc space, greater separation distance can be realized than that for cages bilaterally inserted in a reamed disc space or for cages having a lateral dimension that approximates the height of the cage. This allows the fusion cage 200 to be positioned closer to the peripheral bony ring of the vertebral body, resulting in increased lateral stability and more load distributed at the strongest portions of the adjacent vertebrae. The cage 200 also enables bilateral fusion cage placement in a smaller sized disc space since less lateral width in the disc space is required to accommodate the fusion cages 200.

Another embodiment of a fusion cage is shown in FIGS. 18–22. As discussed above with respect to fusion cage 200, fusion cage 400 is also particularly suited for insertion into an unreamed disc space in either the lumbar or cervical regions of the spine. It is also contemplated that fusion cage 400 may be inserted using the techniques and instruments described herein, among others.

Cage 400 includes body 402 extending between leading end 404 and trailing end 406. One or more threads 408 extend around body 402 between leading end 404 and trailing end 406 transverse to a central axis C. Body 402 defines a number of side apertures 412 in sidewalls 424 that communicate with a hollow interior 414. An end plate 416 is provided at leading end 404. End plate 416 defines a number of openings 418 therethrough communicating with interior 414 to further increase the porosity of cage 400 for fusion. A tapered portion 417 extends from leading end to body 402, and preferably includes a shape that correspond to that of the previously inserted distractor to facilitate insertion of the cage 400 into the disc space. In one specific embodiment, tapered portion 417 is unthreaded and has a length of about 2.5 millimeters.

Figure 22:
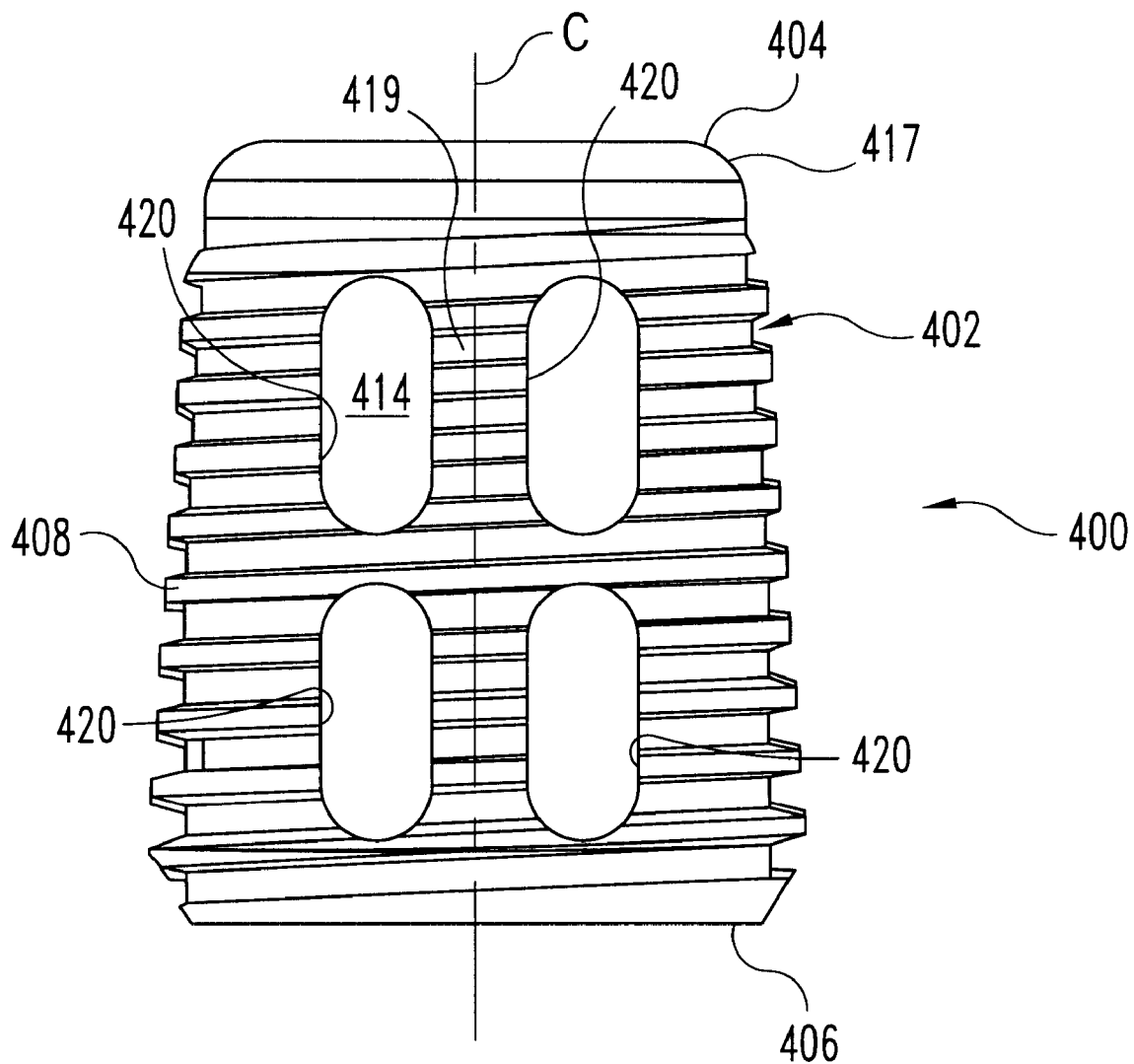
FIG. 22 is a top plan view of the fusion cage of FIG. 18.

As shown in FIG. 22, cage 400 has a top surface 419 that is adjacent the superior vertebral endplate when cage 400 is inserted. At top surface 419 body 402 defines a number of top apertures 420. In a preferred embodiment, there are provided four top apertures 420 that are substantially the same size and symmetrically positioned about axis C. A bottom surface 421 includes a number of bottom apertures 422 corresponding in size, shape and location to top apertures 420. It is desirable that hollow interior 414 be filled with BMP material, bone graft, chips or other bone growth compound to effect fusion between the vertebrae.

For ease of insertion and maintenance in the disc space, it is contemplated that body 402 includes threads 408 along at least a portion of the length of body 402 that are self-tapping. It is also contemplated that threads 408 gradually increase in depth from d1 to d2 as threads 408 run from leading end 404 to trailing end 406. In this embodiment of cage 400, threads 408 have a sloped crest 430 extending between trailing wall 432 and a leading wall 434, forming a substantially rectangular thread profile. As cage 400 is threaded into the disc space, the material harvested by the threads 408 is deposited through openings 420 and 422 and into hollow interior 414. Body 402 is tapered along its length from height H1 at leading end 404 to height H2 at trailing end 406 to define an angle that restores the lordotic angle of the spine when inserted into the disc space. The tapered body 402 further distracts the disc space in accordance with the increase in height associated with the taper of body 402 as cage 400 is threaded into the disc space. As cage 400 is inserted, threads 408 achieve purchase into the intact bony endplates of the adjacent vertebrae. The increase in thread depth from leading end 404 to trailing end 406 allow greater purchase of the threads adjacent trailing end 406 into the bony endplate, thus reducing the risk of cage 400 backing out or un-threading from the disc space. Thus, maintenance of cervical and lumbar lordosis is improved and the risk of subsidence associated with implants inserted into a reamed disc space is eliminated.

Other advantages realized by cage 400 are associated with its relatively smaller size as compared to cages inserted in reamed openings. Since the endplates of the vertebrae are not reamed, the overall heights H1 and H2 of cage 400 are less than that required for a cage inserted into a reamed disc space. Typically, heights H1 and H2 will be about 4 to 6 millimeters less than the corresponding heights of a cage for a reamed disc space. Also, the sidewalls 424 of cage 400 each include a cutout 426 that reduces the lateral dimension of the inserted cage 400. Thus, if two cages 400 are bilaterally inserted into the disc space, greater separation distance can be realized than that for cages bilaterally inserted in a reamed disc space or for cages having a lateral dimension that approximates the height of the cage. This allows the fusion cage 400 to be positioned closer to the peripheral bony ring of the vertebral body, resulting in increased lateral stability and more load distributed at the strongest portions of the adjacent vertebrae. The cage 400 also enables bi-lateral fusion cage placement in a smaller sized disc space since less lateral width in the disc space is required to accommodate the fusion cages 400.

Figure 21:
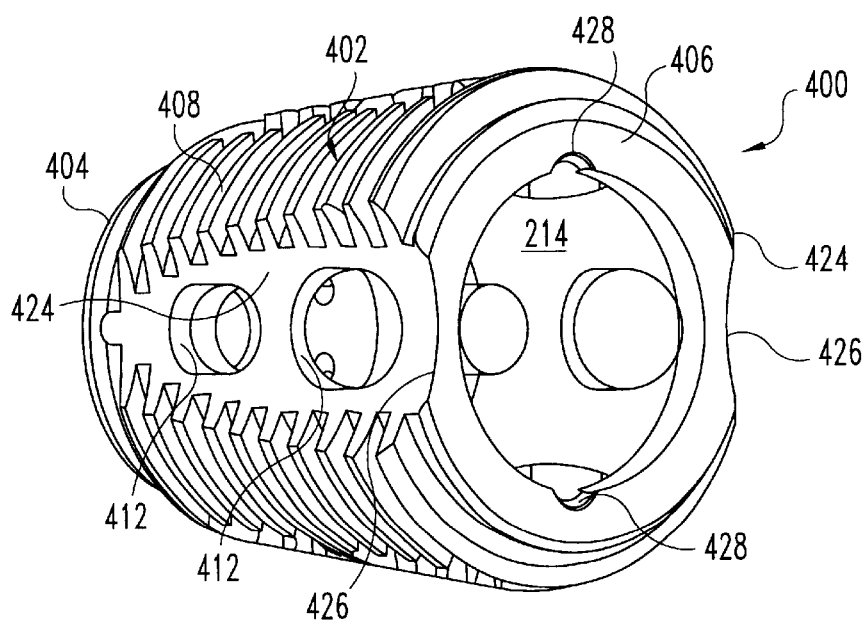
FIG. 21 is a perspective view from the trailing end of the fusion cage of FIG. 18.

In one embodiment, cage 400 includes tool guides 428 at trailing end 406, as shown in FIG. 21. Tool guides 428 are configured to receive and guide the movement of the shaft of an instrument inserted into interior 414 of the cage 400. Cage 200 described above could similarly be provided with such tool guides.

Figure 23:
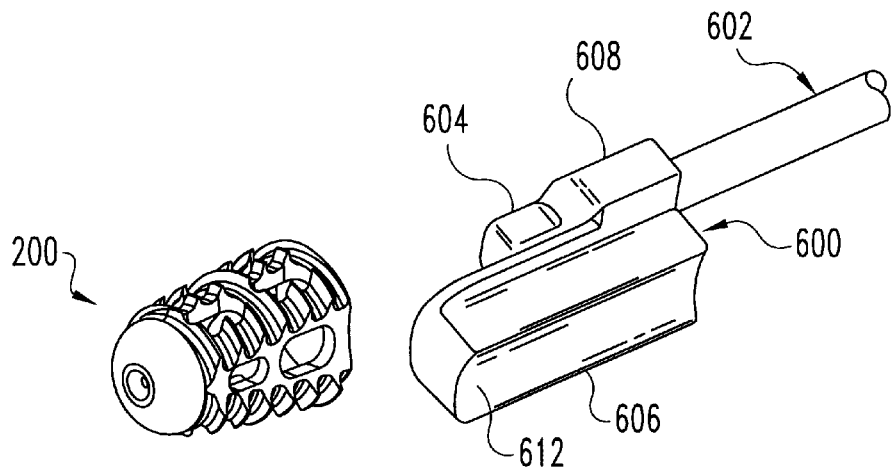
FIG. 23 is a perspective view of a spacer device and fusion cage according to another aspect of the present invention before the spacer device is secured to a fusion cage.
Figure 24:
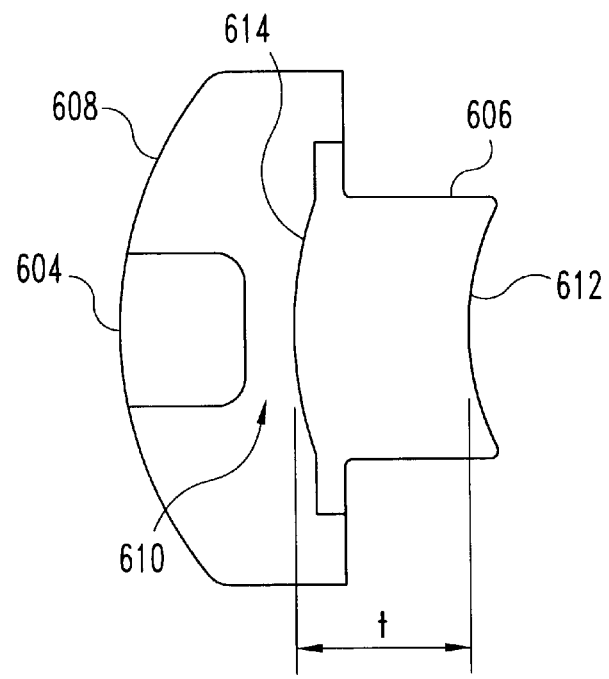
FIG. 24 is a left end elevational view of the spacer device of FIG. 23.
Figure 25A:
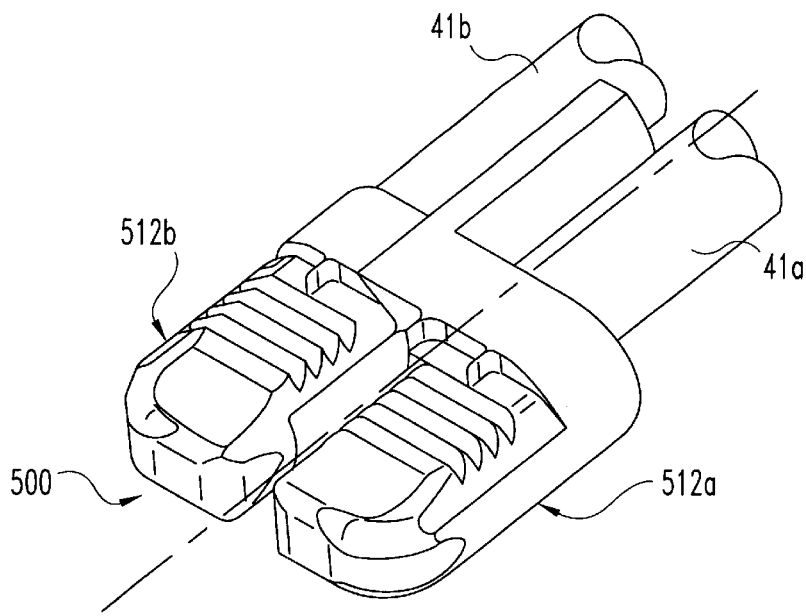
FIGS. 25(a)–25(h) show various steps of a method according to the present invention using instruments and cages of the present invention.
Figure 25B:
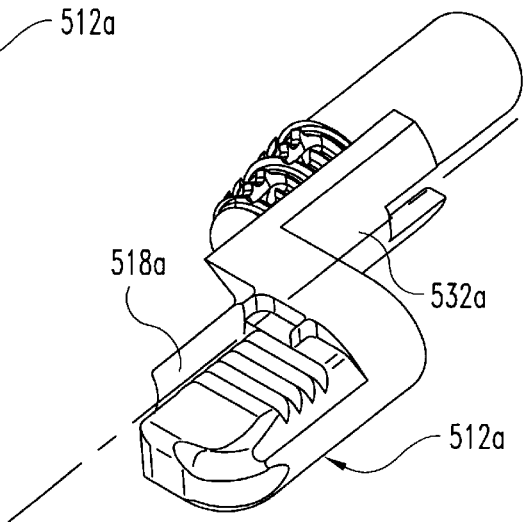
Figure 25C:
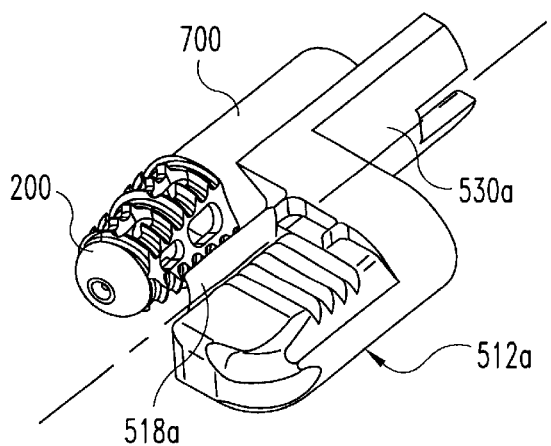
Figure 25D:
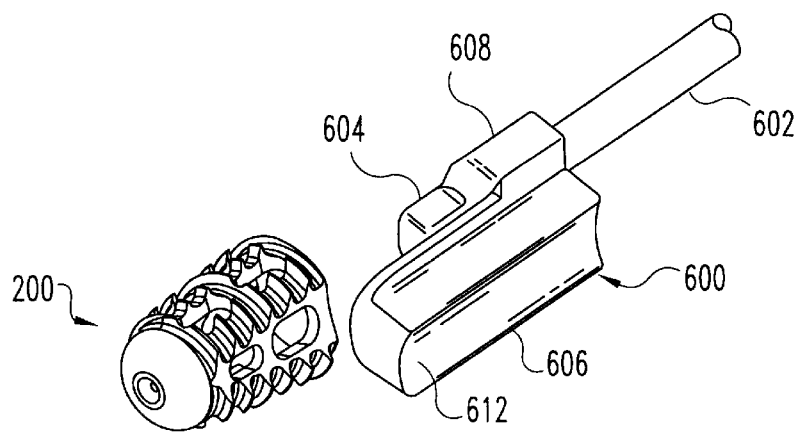
Figure 25E:
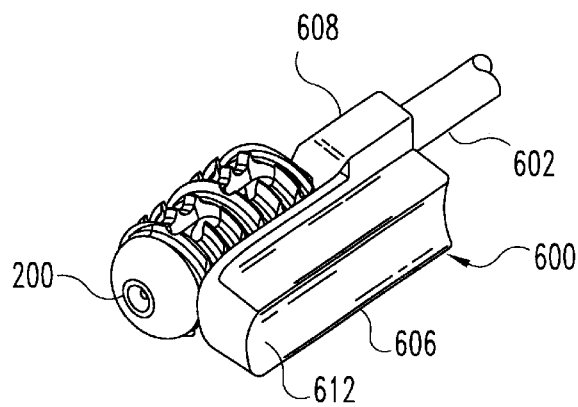
Figure 25F:
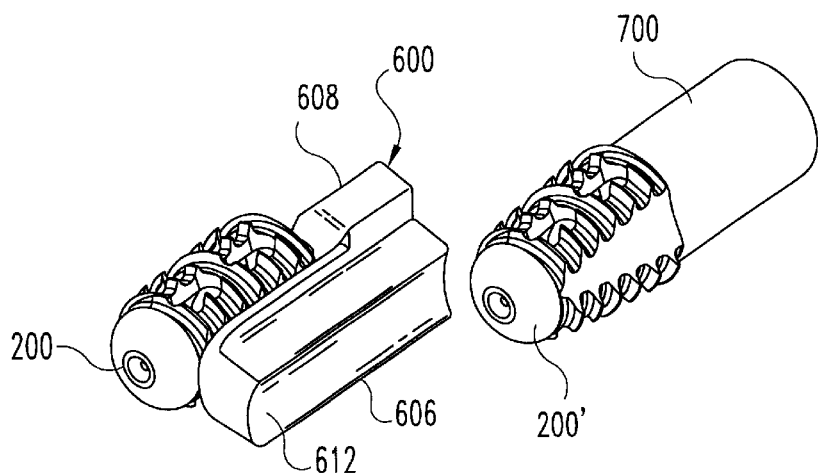
Figure 25G:
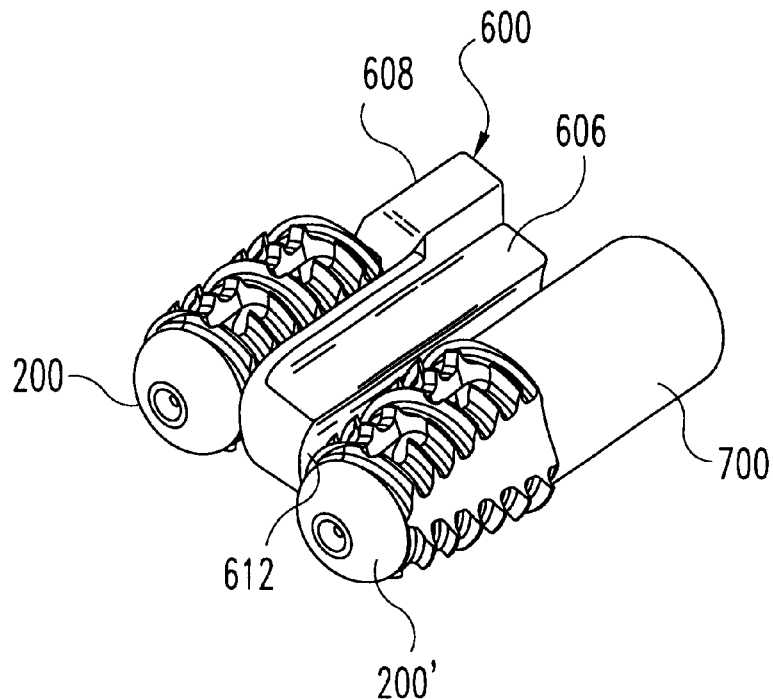
Figure 25H:
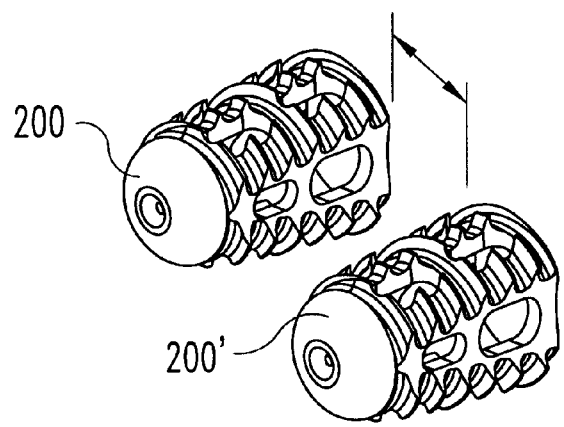

Referring now to FIGS. 23 and 24, there is illustrated a spacer 600 engagable to a spacer insertion shaft 602. Spacer 600 is connectable to a fusion cage, such as the illustrated fusion cage 200, in order to guide and maintain lateral spacing of a second fusion cage (not shown) during insertion of the second cage into the disc space. Spacer 600 includes a cage connector 604 that extends into the hollow interior of cage 200. Preferably, connector 604 has a cross-section shape that fits within the trailing end wall opening of cage 200 such that spacer 600 will be non-rotatably secured to cage 200. Extending proximally from connector 604 is a proximal end portion 608 that includes a proximal end wall with a threaded opening (not shown) to engage spacer 600 to shaft 602. Extending from the medial side of proximal end portion 608 is a spacing member 606 that is separated from connector 604 by gap 610. Gap 610 is sized such that a medial sidewall of cage 200 can fit therein when spacer 600 is connected to the inserted cage 200 with connector 604 in the interior of the cage and spacing member 606 positioned along the sidewall of cage 200. Spacing member 606 has a thickness t that corresponds to the desired spacing between the inserted fusion cages. Spacing member 606 has a concave guide surface 612 along its medial side to guide threaded insertion of the second cage. Spacing member 606 and guide surface 612 preferably extend to the trailing end wall of proximal end portion 608 and outside the disc space to support and guide the shaft of the implant insertion device. Spacing member 606 also includes a convex lateral sidewall that conforms with the concave sidewall of cage 200 to provide a secure and snug fit between cage 200 and spacer device 600. After the second cage is inserted into the disc space, spacer 600 is removed from first cage 200.

Referring now to FIGS. 25(*a*) to 25(*h*), one preferred method according to the present invention will be described with respect to cage 200, distractor assembly 500, and spacer device 600. It will be understood, however, that the other embodiments of cages, spacers, and instruments described herein also have application with the described method. In FIG. 25(*a*) there is illustrated distractor assembly 500 prepared for insertion in the disc space. The disc space is accessed using any known surgical technique, including those which anteriorly approach the disc space through an open incision, through one or more tubes or through a double barrel tube, and through laparoscopic instruments that provide a sealed working channel. The surgical site is prepared for entry of distractor assembly 500, and distractors 512*a* and 512*b* are assembled and positioned adjacent the disc space. Although the distractors can be inserted individually, it is preferred that the proximal ends of the distractor shafts 41*a*, 41*b* are coupled with an impactor cap and distractors 512*a*, 512*b* driven into the disc space simultaneously.

In FIG. 25(*b*) distractor assembly 500 has been inserted and second distractor 512*b* withdrawn. Fusion cage 200 is coupled to inserter shaft 700. Guide arm 532*a* guides insertion of cage 200 to the disc space, and medial portion 518*a* guides cage 200 as it is threaded into the disc space with inserter shaft 700 guided by guide arm 532*a* until cage 200 is threaded to the desired position in the disc space, as shown in FIG. 25(*c*).

In FIG. 25(*d*) first distractor 512*a* is removed and spacer 600 is secured to shaft 602. Connector 604 of spacer 600 is secured to cage 200 with spacing member 606 positioned along the medial side of cage 200 as shown in FIG. 25(*e*). In FIG. 25(*f*) shaft 602 is removed and a second cage 200' is connected to implant inserter shaft 700. Spacing member 606 guides insertion of cage 200' as it is threaded into the disc space as shown in FIG. 25(*g*). As shown in FIG. 25(*h*), spacer 600 is removed from cage 200 and cages 200, 200' are inserted into the disc space and the desired lateral spacing between cages 200, 200' has been achieved.

Figure 26:
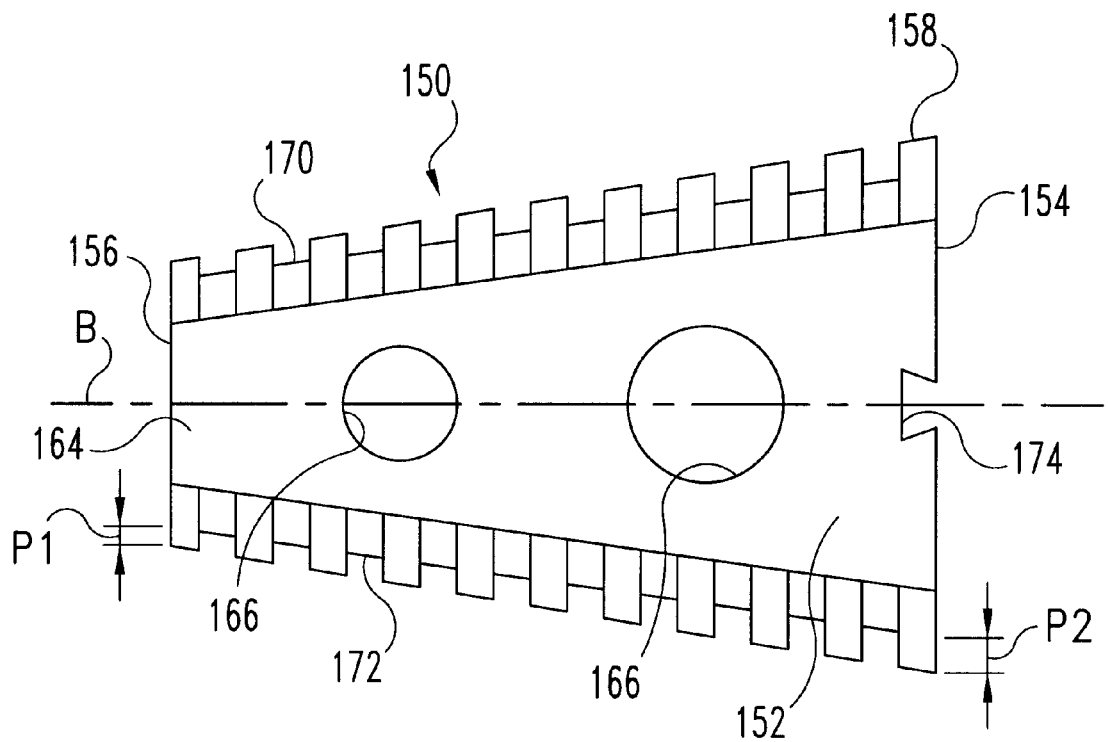
FIG. 26 is a side elevational view of a fusion cage according to another aspect of the present invention.
Figure 27:
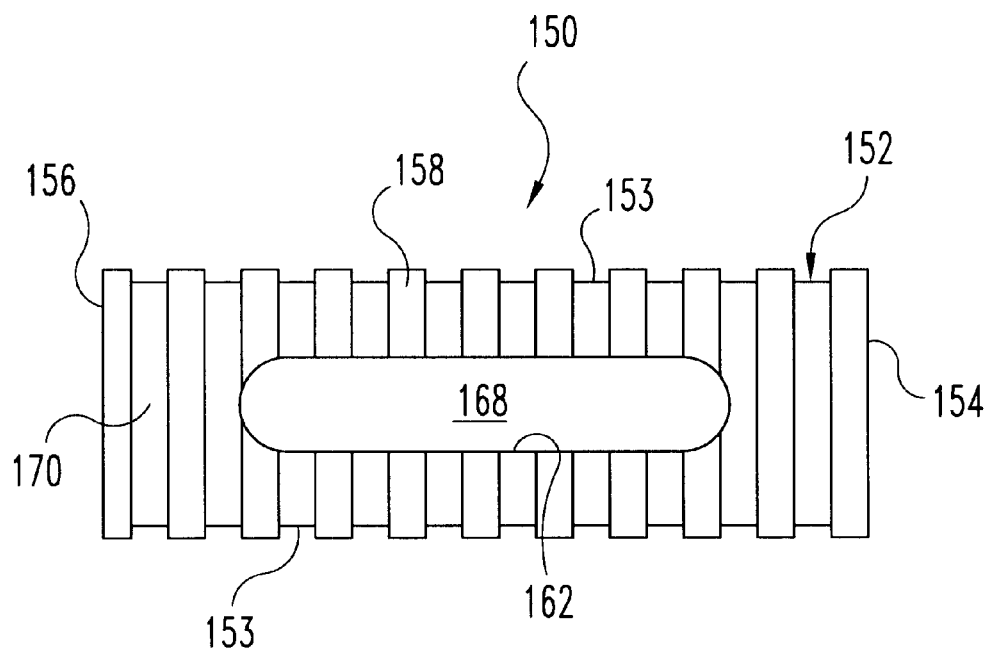
FIG. 27 is a top plan view of the fusion cage of FIG. 26.

In accordance with another aspect of the invention, there is provided in FIGS. 26–27 a fusion cage 150 that is insertable into an unreamed disc space distracted by the distractor assembly of the present invention. While it is contemplated that two fusion cages 150 are bilaterally inserted into the disc space, it is also contemplated that a single fusion cage 150 or more than two fusion cages 150 may be inserted into the unreamed disc space.

Fusion cage 150 includes body 152 extending between trailing end 154 and leading end 156. Body 152 includes a plurality of threads 158 extending at least partially therearound for partially cutting into the thickness of the vertebral endplates. Threads 158 preferably have a depth that increases from p1 at leading end 156 to p2 at trailing end 154. Providing deeper threads towards trailing end 154 increases back-out resistance of cage 150 in the disc space. A cage 150 having threads 158 with a constant depth is also contemplated. Top surface 170 includes upper aperture 162 and bottom surface 172 includes a lower aperture (not shown) communicating with hollow interior 168. A plurality of openings 166 communicating with hollow interior 168 is provided between top surface 170 and bottom surface 172 through sidewalls 153 to increase the porosity of cage 150 for fusion. Trailing end 154 of body 152 may include notch 174. Notch 174 is configured to receive a de-rotation bar (not shown) therethrough. The de-rotation bar is placed in notch 174 of a first fusion cage 150 and extends to a notch of a second fusion cage (not shown) bi-laterally inserted with the first fusion cage 150. The de-rotation bar prevents rotation of the fusion cages in the disc space.

Figure 28:
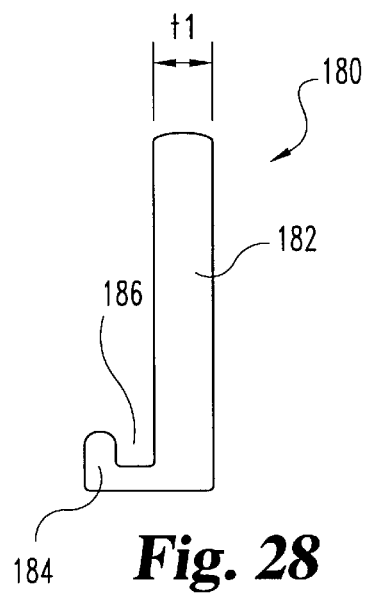
FIG. 28 is a top plan view of another embodiment spacer device according to the present invention.
Figure 29:
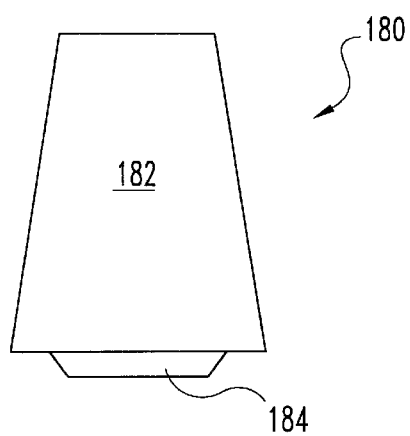
FIG. 29 is a side elevational view of the spacer device of FIG. 28.
Figure 30:
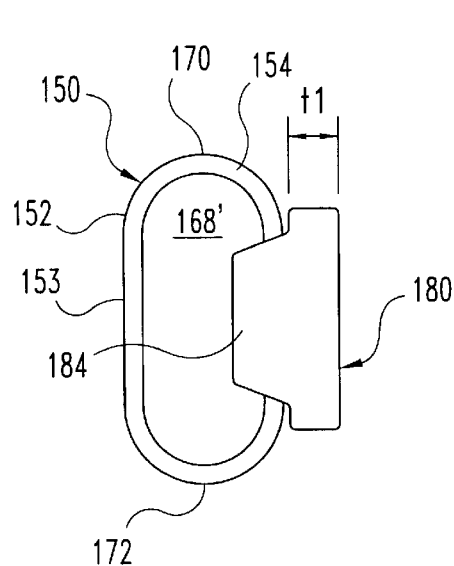
FIG. 30 is an end elevational view of the trailing end of the fusion cage of FIG. 26 with the spacer device of FIG. 28 connected thereto.

In FIGS. 28–29, there is shown another embodiment spacer device 180. Spacer device 180 includes a spacing member 182 having a thickness t1 and a cage connector 184 extending from body portion 182. Spacing member 182 and connector 184 define a recess 186 therebetween. As shown in FIG. 30, after insertion of cage 150 into the disc space, the spacer 180 may be connected to the medial side of cage 150 and used as a guide for bi-lateral placement of a second cage in the disc space. The recess 186 receives a portion of the wall of body 152 at trailing end 154 and connects the spacer 180 with cage 150 along medial sidewall 153. Spacing member 182 extends from trailing end 154 along body 152 for substantially it entire length. The thickness t1 of spacing member 182 is determined by the desired separation distance between the first and second cages.

Another advantage realized by cage 150 is that the portion of the endplate communicating interior 168 through apertures 162 may be removed or reduced to bleeding in order to obtain the advantages associated with implants inserted into a reamed disc space. As described below, a cutting instrument with a curette or burr is inserted into the interior of the inserted cage 100 to remove bony material from the vertebral endplates through the apertures 162 in the top surface 170 and bottom surface 172. The remaining portions of the endplates remain intact and provide a strong bearing surface in contact with body 152 and threads 158. Bone growth material may then be placed in hollow interior 168, and fusion between the vertebrae is attained in a manner realized by a fusion cage inserted into a reamed disc space while retaining the increased stability and load distribution capabilities associated with inserting the fusion cage 150 in an unreamed disc space.

Figure 31:
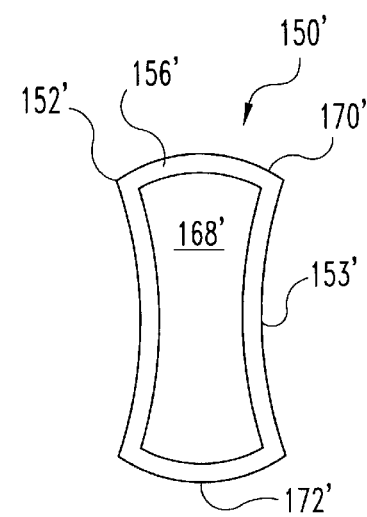
FIG. 31 is an end elevational view of the trailing end of an alternate embodiment of the fusion cage of FIG. 26.

An alternate embodiment cage 150' is shown in FIG. 31. Cage 150' is similar to cage 150, but has sidewalls 153' that curve inwardly between top surface 170' and bottom surface 172'. Spacer device 180 would be shaped accordingly to conform to sidewall 153' to allow connection between spacer device 180 and cage 150'. Thickness t1 of body portion 182 is thus increased due to the concavity of sidewall 153'. A cage 150' having concave sidewalls 153' allows the distraction height and thread depth of the cage to be increased without a corresponding increase in the lateral portion of the disc space occupied by the cage.

Figure 32:
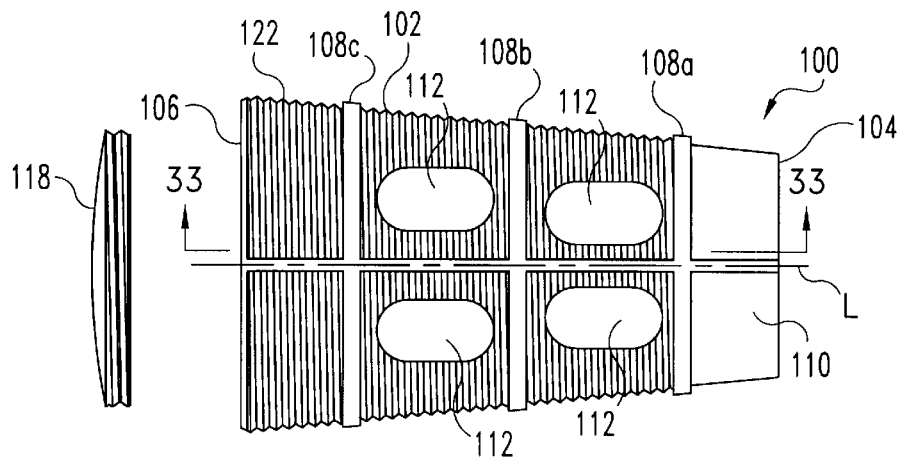
FIG. 32 is a top plan view elevation of a fusion cage according to yet another aspect of the present invention.
Figure 33:
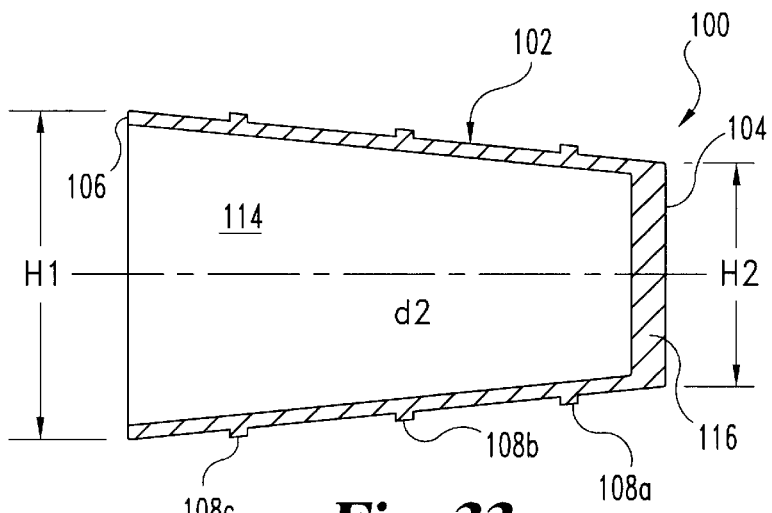
FIG. 33 is sectional view through line 33—33 of FIG. 32.
Figure 34:
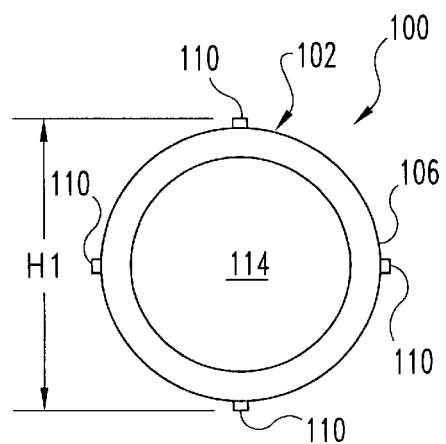
FIG. 34 is an end elevational view of the trailing end of the fusion cage of FIG. 32.

There is provided a further embodiment of a fusion in FIGS. 32–34. Fusion cage 100 is designed for insertion into an unreamed disc space in either the lumbar or cervical regions of the spine. Insertion of cage 100 in an unreamed disc space eliminates the need for a channel discectomy and/or reaming of the disc space prior to insertion of the cage 100. Fusion cage 100 does not require a cannula, guide tube, or laparoscopic instrument for insertion into the disc space, although the use of such instruments and techniques associated therewith are not precluded by cage 100. It is also contemplated that fusion cage 100 may be inserted using the techniques and instruments described herein, among others.

Cage 100 includes body 102 extending between leading end 104 and trailing end 106. A number of struts 108a, 108b and 108c are positioned between ends 104 and 106, and extend transverse to a central axis L of cage 100 around body 102. A longitudinal strut 110 extends along axis L between ends 104 and 106 along body 102. Although only one strut 110 is shown in FIG. 13, it is contemplated that additional struts 110 are positioned about body 102 along axis L. Struts 108 and 110 strengthen and support body 102. Body 102 defines a number of large openings 112 that communicate with a hollow interior 114. A blunt nose 116 is provided at leading end 104. Blunt nose 116 pushes disc material from leading end 104 and around body 102 as cage 100 is inserted. A cap 118 may be placed on trailing end 106 to close hollow interior 114. It is desirable that hollow interior 114 be filled with BMP material, bone graft, chips or other bone growth compound to effect fusion between the vertebrae before placement of end cap 118. Cap 118 may be threaded to mate with corresponding threads formed at end 106 in the interior 114 of body 102, or cap 118 may be press fit into hollow interior 114 at end 106.

For ease of insertion, it is contemplated that body 102 includes one or more threads 122 therearound along at least a portion of the length of body 102. Preferably, the material harvested by the threads 122 of body 102 is deposited through openings 112 and into hollow interior 114. Body 102 is tapered along its length from height H1 at trailing end 106 to height H2 at leading end 104 to define an angle that corresponds to the lordotic angle of the spine when inserted into the disc space. The blunt nose 116 and strengthened tapered body 102 distract the disc space as cage 100 is inserted therein, thus completely or assisting in distracting the disc space. As cage 100 is inserted, the threads 122 achieve purchase into the intact bony endplates of the adjacent vertebrae. Thus, maintenance of cervical and lumbar lordosis is improved by eliminating the risk of subsidence associated with an implant inserted into a reamed disc space. The cage 100 is also inserted in a position that accommodates the anatomy of the disc space since the cage 100 is self-directed as it is inserted therein.

Other advantages realized by cage 100 are associated with its relatively smaller size as compared to cages inserted in reamed openings. Since the endplates of the vertebrae are not reamed, the overall heights H1 and H2 of cage 100 are less than that required for a cage inserted into a reamed disc space. Typically, heights H1 and H2 will be about 4 to 6 millimeters less than the corresponding heights of a cage for a reamed disc space. Thus, if two cages 100 are to be inserted bilaterally into the disc space, greater separation distance can be realized than that for cages bilaterally inserted in a reamed disc space. This allows the fusion cage 100 to be positioned closer to the peripheral bony ring of the vertebral body, resulting in increased lateral stability and more load distributed at the strongest portions of the adjacent vertebrae.

Figure 35:
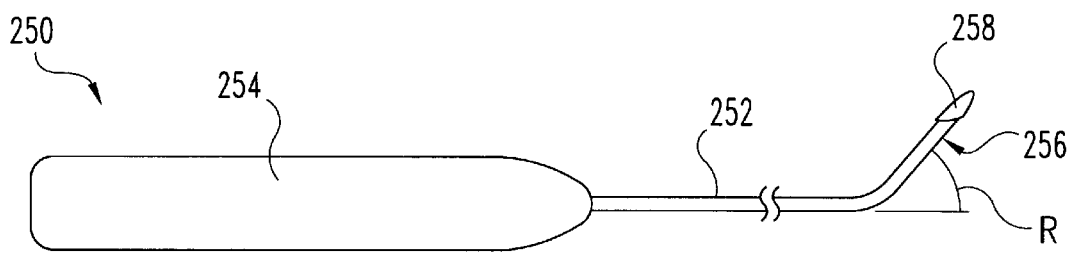
FIG. 35 is a side elevational view of a surgical instrument according to another aspect of the present invention.
Figure 36:
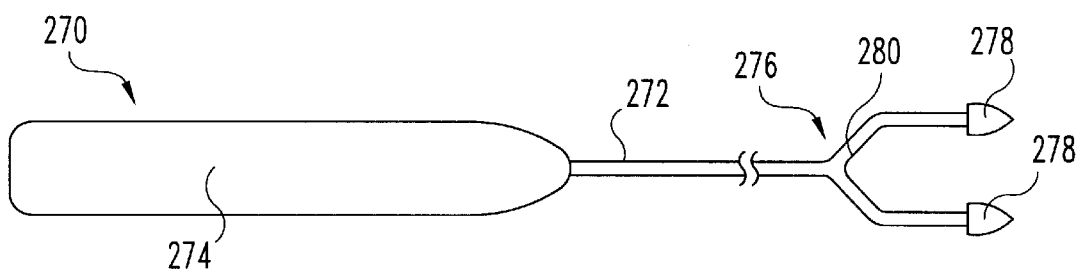
FIG. 36 is a top plan view of an alternate embodiment of the surgical instrument of FIG. 35.
Figure 37:
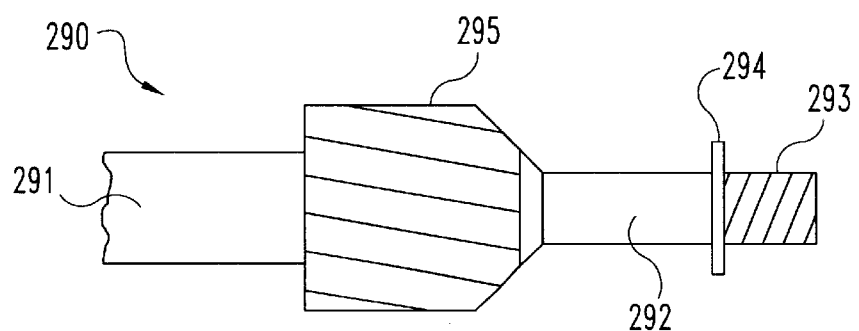
FIG. 37 is a partial elevational view of a surgical instrument according to yet another aspect of the present invention.

In accordance with a further aspect of the invention, various instruments are provided for disc space and vertebral endplate preparation, as shown in FIGS. 35–37. In FIG. 35, cutting instrument 250 includes a shaft 252 extending from handle 254 to a distal portion 256. Preferably, distal portion 256 is deflected at an angle R with respect to shaft 252. A curette or blade 258 is positioned on the end of distal portion 256. Blade 258 is sharpened and configured to remove bone material from the vertebral endplates upon application of a force applied through handle 254 by the surgeon. Shaft 252 and distal portion 256 extend into a fusion cage inserted in the disc space, such as the cage 100 or 150 described above, or the cage 200 described below. Blade 258 extends from the interior of the cage through openings in the fusion cage, such as openings 162 of cage 150; the openings 112 of cage 100; or the openings 220 of cage 200. The blade 258 contacts the portion of the vertebral endplate communicating with the openings in the cage.

Cutting instrument 250 provides an instrument that allows the surgeon to remove bony material from the endplates of the vertebral bodies after the fusion cage is inserted into the disc space. Subsidence and settling of the implant into the adjacent vertebrae is avoided since the body of the fusion cage is fully supported by the remaining bony material of the endplates. As realized in procedures that utilize a reamed disc space, superior fusion may be achieved by removing the bony endplates to promote bone growth between the vertebral bodies through the fusion implant. However, the instruments of the present invention remove a portion of the bony endplates only at the areas where the endplates communicate with the opening in the cage.

FIG. 36 is an alternate embodiment cutting instrument 270 having a shaft 272 extending from handle 274. A distal portion 276 of shaft 272 is deflected upward and an angle R with respect to the shaft, as described above with respect to curette 250. Cutting instrument 270 is identical to cutting instrument 250, except that distal portion 276 includes a forked portion 280 having a pair of blades 278. Blades 278 are preferably laterally spaced from one another. Cutting instrument 270 has particular application to a fusion cage having a pair of holes communicating with the vertebral endplate that are laterally adjacent one another. See, for example, apertures 112 of fusion cage 100 and apertures 220 of fusion cage 200 (described below.) Cutting instrument 270 allows the surgeon to simultaneously and uniformly remove bony material through adjacent holes in the fusion cage.

The present invention also contemplates that cutting instruments 250 and 270 include a mechanical burr or reciprocating blade in place of blades 258 and 278. The instruments 250 and 270 include circuitry and a motor for connection to a power source that drives the mechanical burr to remove bony material from the endplates.

One preferred technique using these instruments will be describe with respect to cage 400, It being understood that the technique could similarly be used with the other cages described herein or other cages known in the art. Cutting instruments 250 or 270 is inserted into cage 400 and used to prepare the vertebral endplates, as discussed above, through top apertures 420 and bottom apertures 422. The guides 428 receive the shaft 252 or 272 to facilitate endplate preparation by maintaining the positioning of the cutting instruments 250, 270 as it is manipulated within the fusion cage. The guide also allows the shaft to bear securely therein so the force applied by the surgeon to the vertebral endplates with blades 258, 278 may be increased.

FIG. 37 is a partial elevational view of another instrument of the present invention. Channel starter 290 is used to prepare a channel through the anterior lip of the vertebral endplates at the disc space portion adjacent trailing end 24 when distractor 12 is positioned therein. Channel starter 290 includes an outer shaft 291 and an inner shaft 292. A cutting blade 295 is positioned between outer shaft 291 and inner shaft 292. Inner shaft 292 has an end portion 293 that is preferably threaded and configured to be received within threaded opening 20 of distractor 12. Inner shaft 294 acts as a guide for the outer shaft 291 and cutting blade 295. A stop 294 is positioned on inner shaft 292 and contacts trailing end 24 to limit insertion of cutting blade 295 to a predetermined depth within anterior portion of the disc space. Cutting blade 295 removes a portion of the endplate thickness at the anterior lip of the vertebral bodies, thus forming a starting channel in the disc space coextensive with the distractor channel formed in the disc space by body portion 14 of distractor 12. The starting channel facilitates insertion of the fusion cage in the disc space by providing a directional guide for insertion of the leading end of the cage. The starting channel also maintains alignment of the body of the fusion cage throughout its insertion.

It is contemplated that the fusion cages of the present invention may be inserted using the techniques and instruments described herein. However, other known techniques and instruments may also be used to insert these cages. The cages of the present invention may be inserted as a single cage in the disc space. The cages of the present invention can also be inserted bi-laterally such that the bi-laterally inserted cages have no spacing therebetween. Further, the cages can be inserted bilaterally and provided with concave sidewalls so that the bi-laterally inserted cages overlap and provide a negative spacing.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. An apparatus for distracting a spinal disc space for insertion of at least one implant in an unreamed disc space, the apparatus comprising:
   a first distractor; and
   a second distractor insertable in side-by-side relation with said first distractor in the disc space, said second distractor including a medially extending portion having a guide surface abutting said first distractor to maintain a spacing between said first and second distractors as said first and second distractors are inserted into the disc space.

2. The apparatus of claim 1, wherein said first and second distractors have a central axis extending therethrough when in said side-by side relation and said guide surface is offset towards said first distractor from said central axis.

3. The apparatus of claim 1, wherein said guide surface of said medially extending portion guides the insertion of the at least one implant into a distraction channel formed in the unreamed disc space after withdrawal of said first distractor.

4. The apparatus of claim 1, wherein:
   said first distractor includes a body portion having a length extending between a leading end and a trailing end, said first distractor including a connecting portion extending from said trailing end of said body portion; and
   said second distractor includes a body portion having a length extending between a leading end and a trailing end, said second distractor including a connecting portion extending from said trailing end of said body portion, said connecting portion of said second distractor including a guide member extending proximally therefrom.

5. The apparatus of claim 4, wherein said guide member includes a notch formed in a proximal end thereof, and said connecting portion of said first distractor includes an extension member having a protrusion positionable in said notch.

6. The apparatus of claim 4, wherein said guide member includes a guide surface aligned with said guide surface of said medially extending portion.

7. The apparatus of claim 6, wherein said guide surface of said medially extending portion and said guide surface of said guide member each have a concave shape.

8. The apparatus of claim 1, wherein each of said first and second distractors includes a body portion having a length extending between a leading end and a trailing end, said body portions having a height between an upper surface and a lower surface sufficient to distract the disc space to a desired disc space height.

9. The apparatus of claim 8, wherein said medially extending portion of said second distractor is integrally formed with said body portion.

10. The apparatus of claim 8, wherein said medially extending portion has a height less than the height of said body portion of said second distractor.

11. The apparatus of claim 8, wherein each of said body portions have a height that is substantially the same as the height of the leading end of the at least one implant.

12. The apparatus of claim 8, wherein said leading end of said body portion is tapered to facilitate insertion of said distractor into the disc space.

13. The apparatus of claim 8, wherein said upper and lower surfaces include notches formed along at least a portion of said length of said body portion.

14. The apparatus of claim 8, wherein said medially extending portion extends from said trailing end along said length of said body portion of said second distractor to a position proximate said leading end of said second distractor.

15. The apparatus of claim 14, wherein said medially extending portion extends along said body portion about three-fourths of said length of said body portion.

16. The apparatus of claim 8, wherein each of said first and second distractors include a connecting portion extending proximally from said trailing end, said connecting portion having a height between a top surface and a bottom surface that is greater than said height of said body portion of said first and second distractors.

17. The apparatus of claim 16, wherein each of said connecting portions includes at least one anchoring member extending towards said leading end of said body portion along one of said upper or lower surfaces of said body portion.

18. A distractor assembly for performing a surgical procedure in a spinal disc space, the distractor assembly having a central axis extending therethrough, said distractor assembly comprising:
   first distractor insertable in the disc space at a first implant location offset to a first side of the central axis;
   a second distractor positionable adjacent said first distractor and insertable in the disc space at a second implant location is offset to a second side of the central axis, said second distractor having a guide surface adjacent said first distractor, wherein said guide surface is offset a distance from the central axis towards said first distractor.

19. The distractor assembly of claim 18, further comprising a first shaft removably attached to said first distractor and a second shaft removably attached to said second distractor.

20. The distractor assembly of claim 18, wherein said second distractor includes a medially extending portion forming said guide surface.

21. The distractor assembly of claim 20, wherein each of said first and second distractors includes a body portion having a length extending between a leading end and a trailing end, said body portions having a height sufficient to distract the disc space to a desired disc space height.

22. The distractor assembly of claim 21, wherein said medially extending portion has a height less than the height of said body portion of said second distractor.

23. The distractor assembly of claim 21, wherein said medially extending portion extends from said trailing end of said second distractor to a position proximate said leading end of said second distractor.

24. A method for distracting a disc space, comprising:

providing a first distractor having a medial portion with a guide surface extending along said first distractor;

providing a second distractor;

assembling the first and second distractors with the second distractor abutting the guide surface to form a distractor assembly, the distractor assembly having a central axis with said guide surface of said first distractor offset from said central axis; and inserting the distractor assembly into the disc space.

25. The method of claim 24, further including preparing a starter channel at the anterior lip of the disc space adjacent a distractor insertion location for each of the first and second distractors.

26. The method of claim 24, further comprising removing the second distractor from the disc space to form a distraction channel in the disc space at a first distractor location.

27. The method of 26, further comprising:

providing a fusion cage having a trailing end wall opening and a leading end with a spacing height approximating a distracted disc space height provided by inserting the distractor assembly into the disc space; and inserting the fusion cage in disc space along the guide surface to maintain lateral positioning of the fusion cage in the disc space.

28. The method of claim 27, further comprising:

removing the first distractor; and inserting a spacer into the trailing end wall opening of the fusion cage, the spacer having a spacing member positionable outside the fusion cage along a medial sidewall of the fusion, the spacing member having a guide surface opposite the fusion cage.

29. The method of claim 28, further comprising:

providing a second fusion cage having a leading end with a spacing height approximating the distracted disc space height; and inserting the second fusion cage in disc space along the guide surface of the spacing member to maintain lateral positioning of the second fusion cage in the disc space.

30. The method of claim 29, wherein the inserted fusion cages each include at least one opening providing communication between a hollow interior of the cage and an adjacent vertebral endplate and further comprising removing bony material from the adjacent vertebral endplate through the opening.

31. The method of claim 30, further comprising placing bone growth material in the hollow interior of the fusion cages.

* * * * *

UNITED STATES PATENT AND TRADEMARK OFFICE
CERTIFICATE OF CORRECTION

PATENT NO.     : 6,582,437 B2
DATED          : June 24, 2003
INVENTOR(S)    : John D. Dorchak et al.

It is certified that error appears in the above-identified patent and that said Letters Patent is hereby corrected as shown below:

<u>Title page,</u>
Item [75], please add as inventor #4 -- Bret M. Berry, Cordova, TN (US) --.

Signed and Sealed this

Twenty-eighth Day of October, 2003

JAMES E. ROGAN
*Director of the United States Patent and Trademark Office*